(12) United States Patent
Davis

(10) Patent No.: US 11,041,845 B2
(45) Date of Patent: Jun. 22, 2021

(54) MOLECULAR DETECTION AND COUNTING USING NANOPORES

(71) Applicant: Roche Sequencing Solutions, Inc., Pleasanton, CA (US)

(72) Inventor: Randall Davis, Pleasanton, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 0 days.

(21) Appl. No.: 16/383,377

(22) Filed: Apr. 12, 2019

(65) Prior Publication Data

US 2019/0250142 A1  Aug. 15, 2019

Related U.S. Application Data

(63) Continuation of application No. PCT/EP2017/076152, filed on Oct. 13, 2017.

(60) Provisional application No. 62/407,986, filed on Oct. 13, 2016.

(51) Int. Cl.
| *G01N 33/487* | (2006.01) |
| *C12Q 1/6844* | (2018.01) |
| *C12Q 1/6851* | (2018.01) |
| *C12Q 1/6806* | (2018.01) |
| *C12Q 1/6813* | (2018.01) |
| *C12Q 1/686* | (2018.01) |

(52) U.S. Cl.
CPC ..... *G01N 33/48721* (2013.01); *C12Q 1/6806* (2013.01); *C12Q 1/686* (2013.01); *C12Q 1/6813* (2013.01); *C12Q 1/6844* (2013.01); *C12Q 1/6851* (2013.01); *C12Q 2600/16* (2013.01)

(58) Field of Classification Search
CPC ............. G01N 33/48721; C12Q 1/6844
See application file for complete search history.

(56) References Cited

U.S. PATENT DOCUMENTS

| 2003/0104428 | A1 | 6/2003 | Branton et al. |
| 2006/0263789 | A1 | 11/2006 | Kincaid |
| 2007/0190543 | A1 | 8/2007 | Livak |
| 2007/0196849 | A1* | 8/2007 | Spier ............... C12Q 1/6827 435/6.16 |
| 2013/0244340 | A1 | 9/2013 | Davis et al. |
| 2013/0264207 | A1 | 10/2013 | Ju et al. |
| 2014/0134616 | A1 | 5/2014 | Davis et al. |
| 2015/0284712 | A1* | 10/2015 | Kurihara ........... C12N 15/1065 506/26 |
| 2017/0136458 | A1* | 5/2017 | Dunne ............... C12Q 1/6874 |

FOREIGN PATENT DOCUMENTS

| GB | WO 2015/124935 | * | 8/2015 |
| WO | 2007/146158 A1 | | 12/2007 |
| WO | 2012/003330 A2 | | 1/2012 |
| WO | 2012/135658 A2 | | 10/2012 |
| WO | WO 2016/145416 | * | 9/2016 |

OTHER PUBLICATIONS

International Search Report and Written Opinion dated Apr. 11, 2018 in connection with PCT/EP2017/076152 filed Oct. 13, 2017, pp. 1-20.
Kumar et al, PEG-Labeled Nucleotides and Nanopore Detection for Single Molecule DNA Sequencing by Synthesis, Scientific Reports, 2012, pp. 1-8, vol. 2.
Robertson et al, Single-molecular mass spectrometry in solution using a solitary nanopore, PNAS USA, May 15, 2007, pp. 8207-8211, vol. 104, No. 20.

\* cited by examiner

*Primary Examiner* — Narayan K Bhat
(74) *Attorney, Agent, or Firm* — Jennifer Rosenfield

(57) ABSTRACT

Provided herein are methods and compositions for detecting and/or quantitating target analytes, including nucleic acids and polypeptides, using nanopore detectable barcodes.

12 Claims, 24 Drawing Sheets

Specification includes a Sequence Listing.

FIG. 2
(A) XYZ barcode - predicted pattern
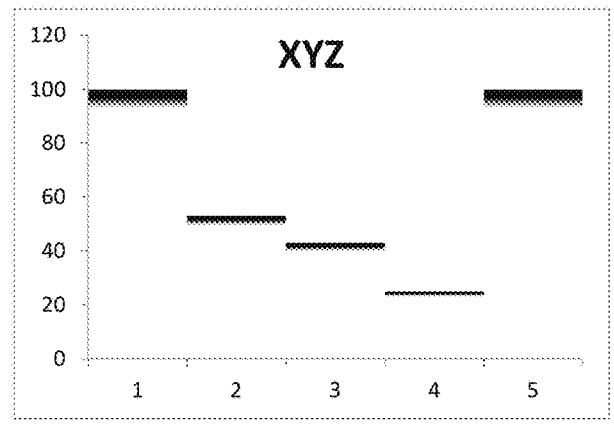
(B) XYZ barcode - Nanopore detected pattern
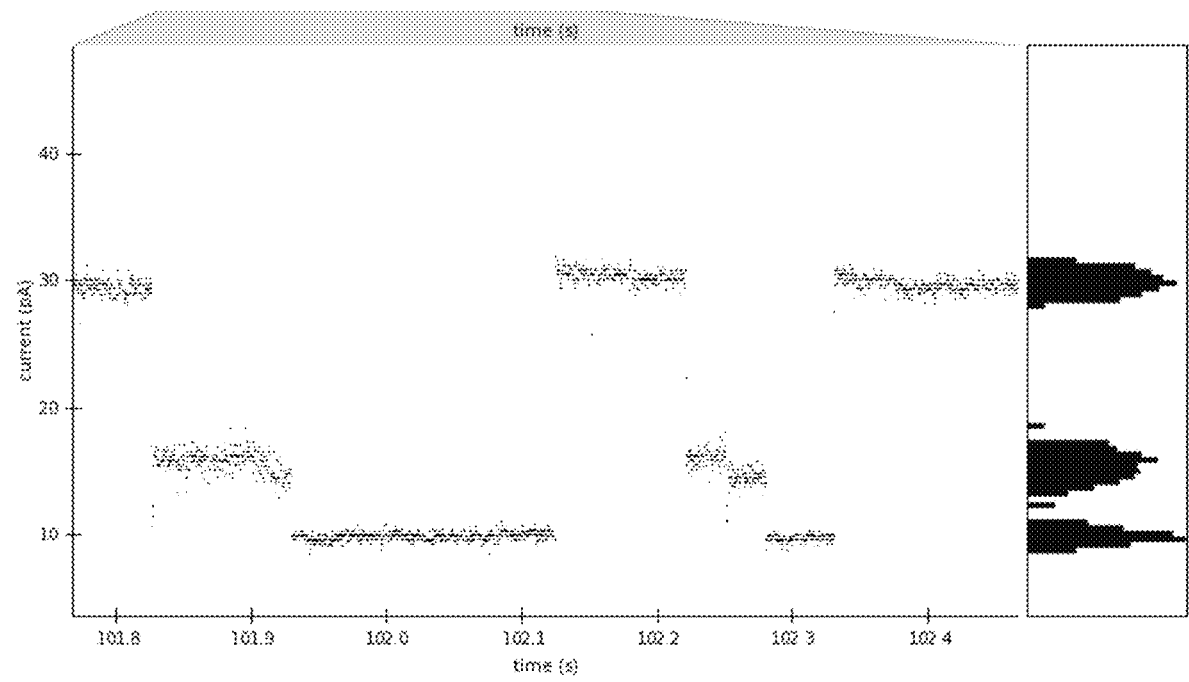

FIG. 3
(A) WYZ Barcode - Predicted Pattern
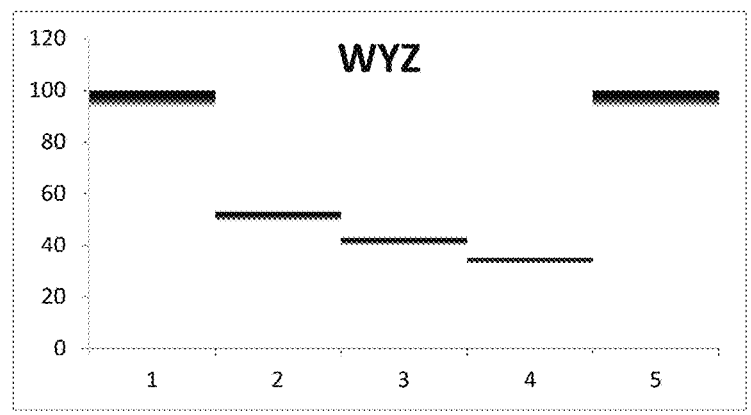
(B) WYZ barcode - Nanopore detected pattern (expt. 1)
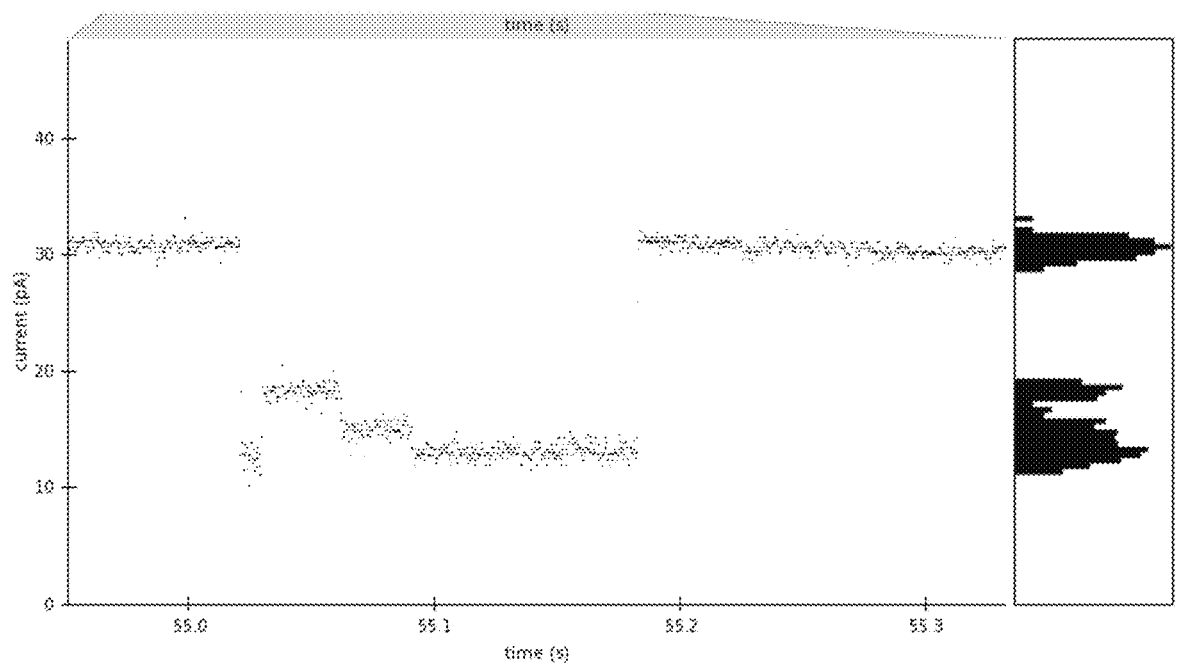

FIG. 4
(A) WXZ Barcode - Predicted Pattern
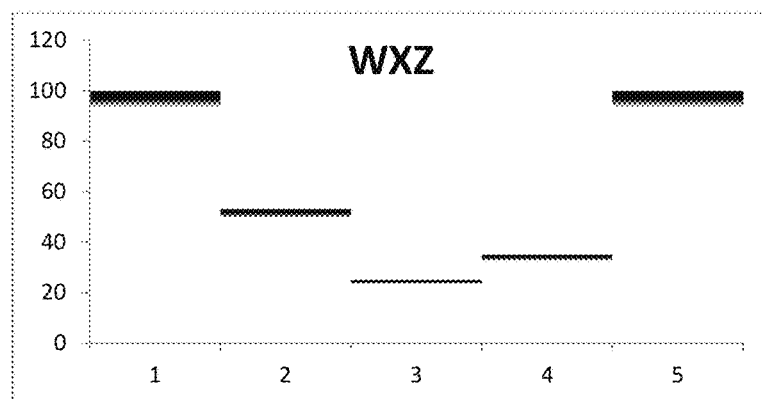
(B) WXZ barcode - Nanopore detected pattern
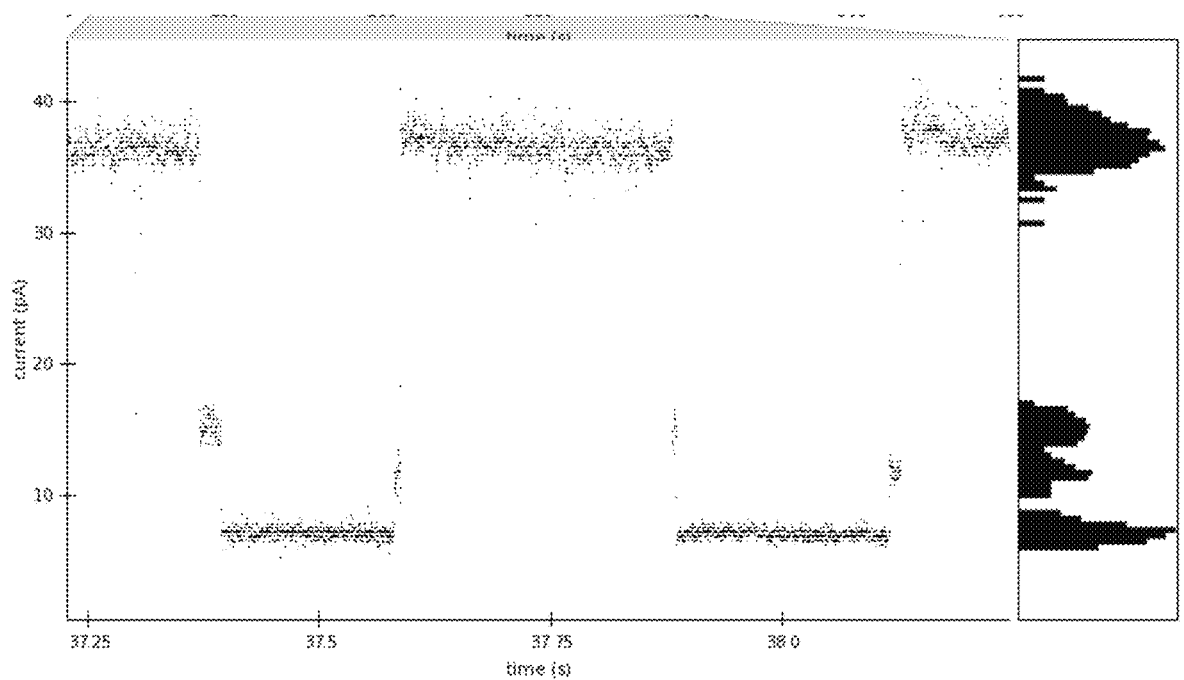

FIG. 5E
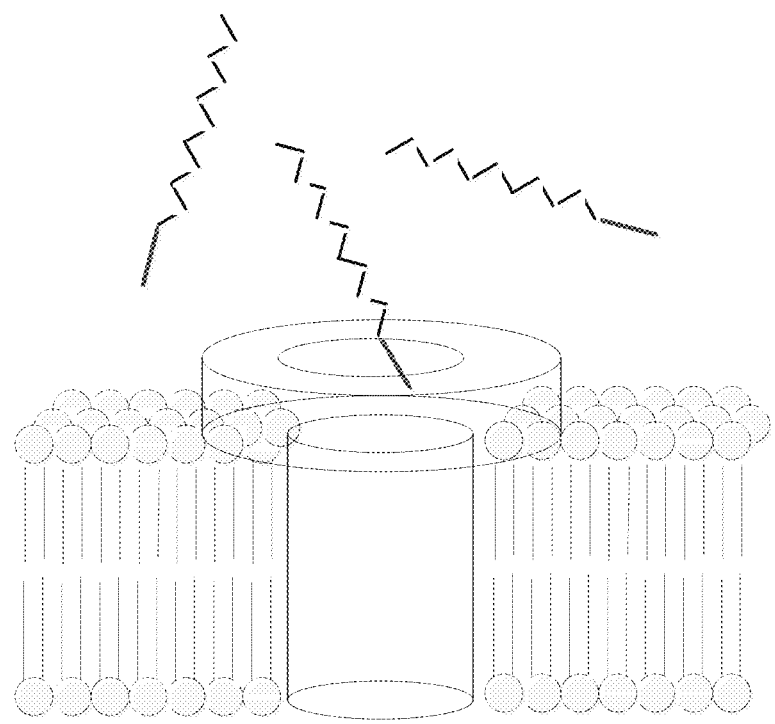
Pull Barcode through Pore, Detect and Read
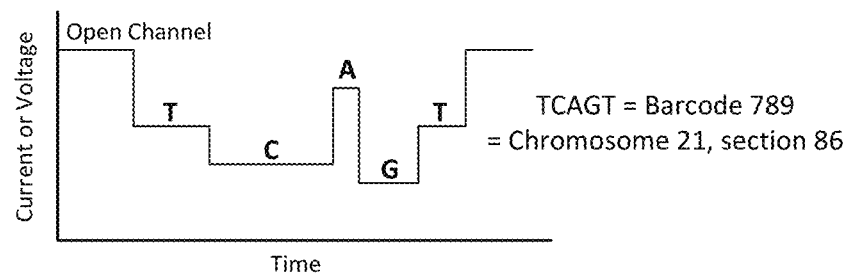
TCAGT = Barcode 789
= Chromosome 21, section 86

FIG. 7
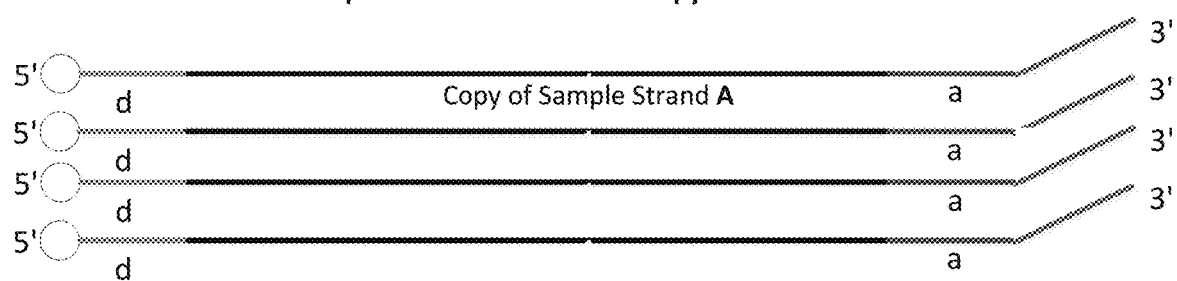
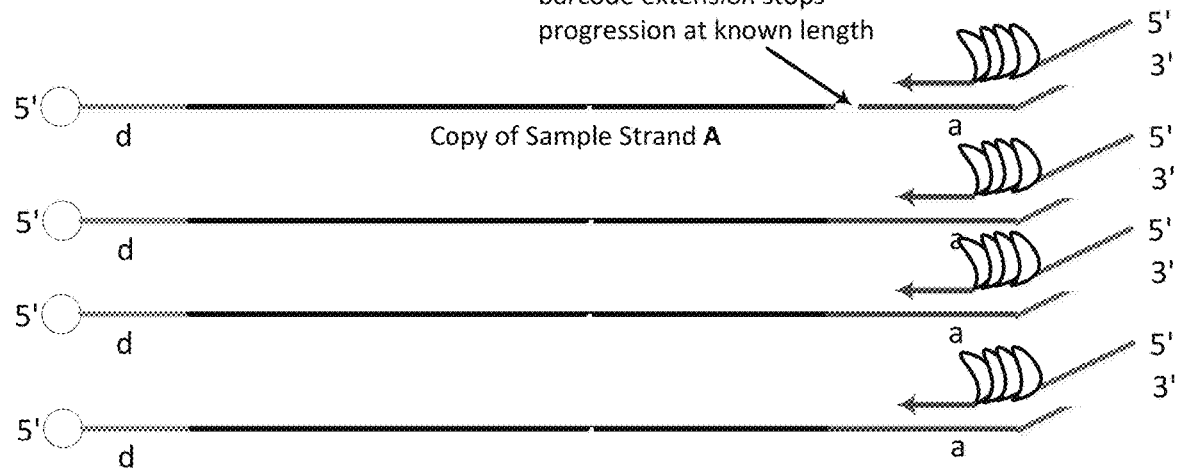

FIG. 8
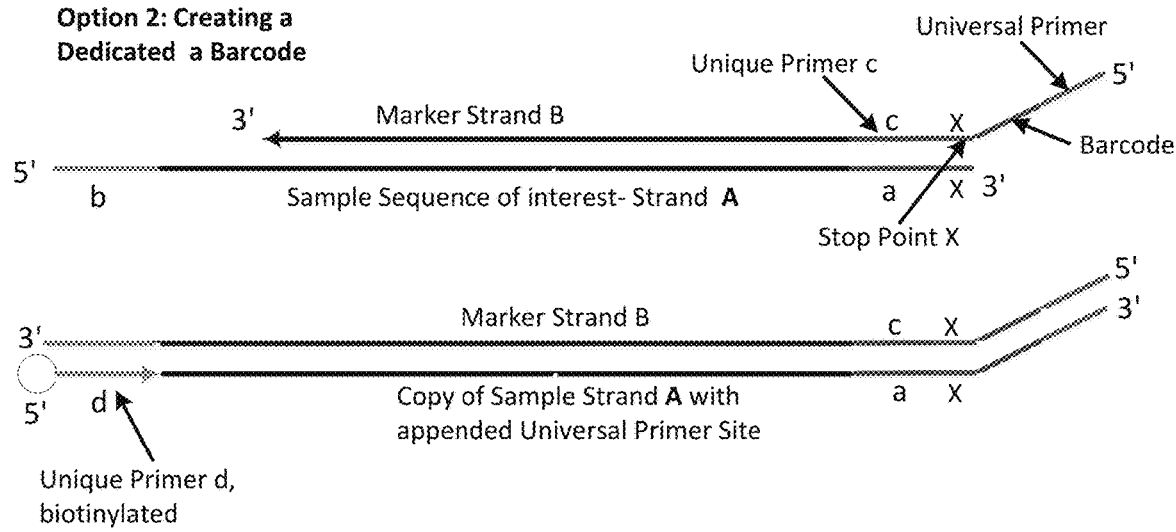
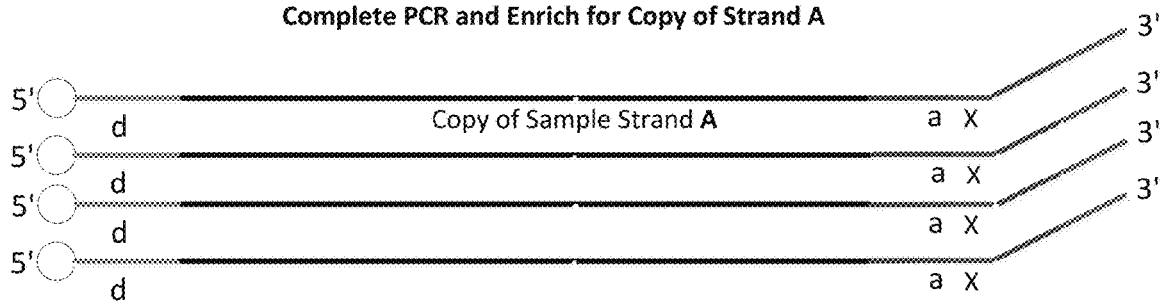

FIG. 11
Complete PCR and Capture Full Marker Strand, Wash out Unreacted Products
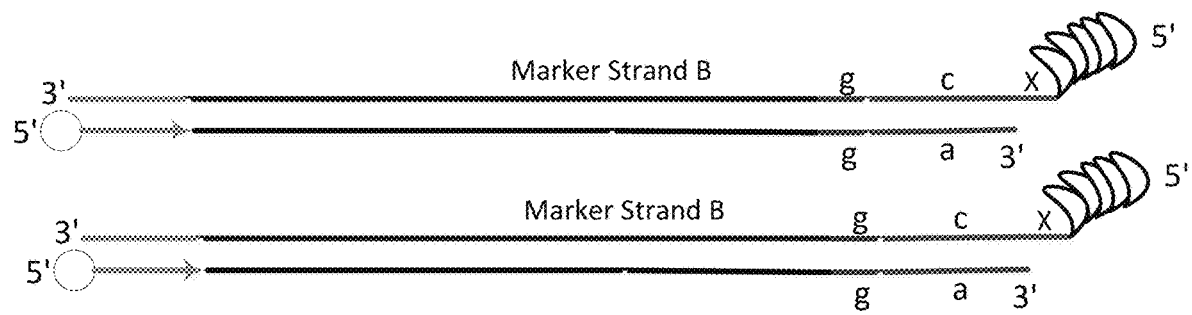
Chemically Release Primer and Barcode from Marker Strand,
Expand Barcode or Hybridize Bumps to Barcode
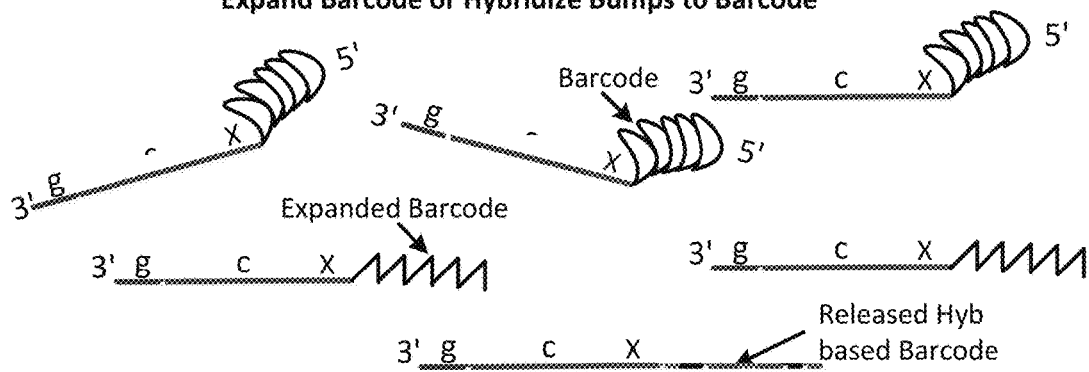

FIG. 12
mRNA Primer Example
Direct to Barcode
Stop Extension at approximate barcode length by raising temperature at appropriate time point (3' UTR may not be unique enough)....
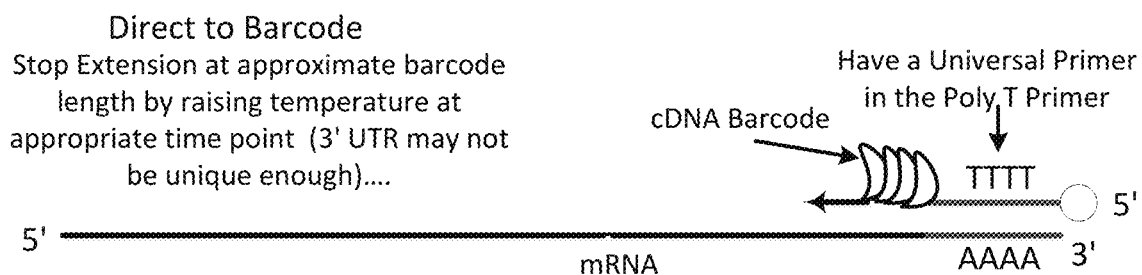
cDNA Synthesis
Enrich for amplified cDNA Sense strands
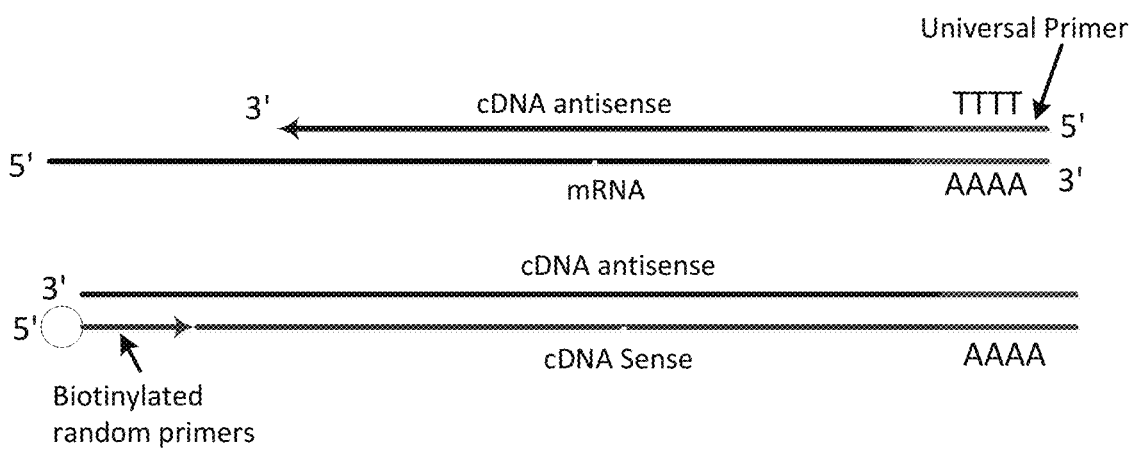

FIG. 15
Enrich for cDNA Sense Strand using biotin label
Extension from Site Specific Primer to Create Barcode
Stop Extension at approximate barcode
length by raising temperature at
appropriate time point
Primer crosses Exon-Intron Boundary
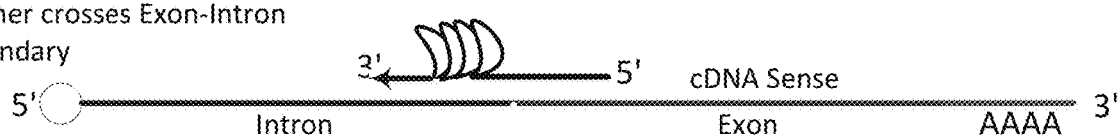
Primer Extends into Possible Intron
Primer in Exon- Simple Detection

FIG. 19

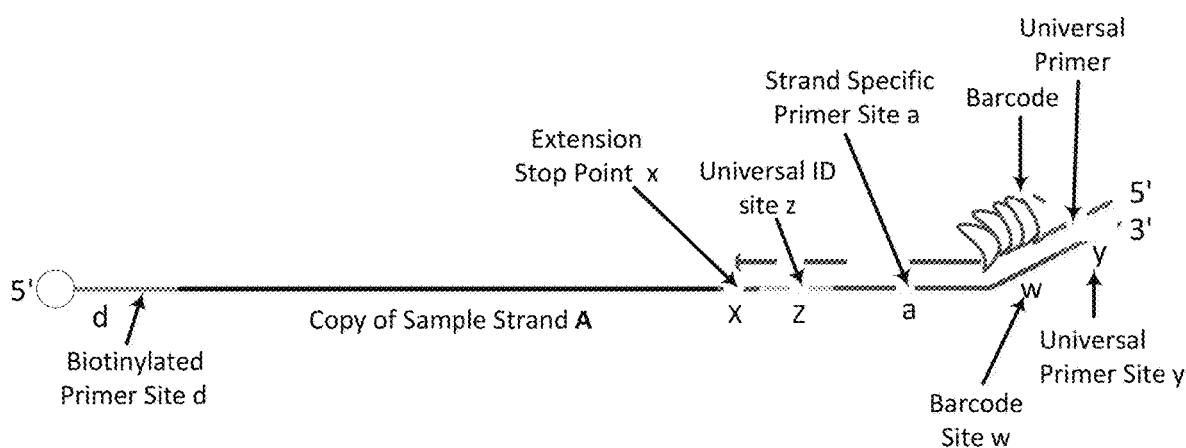

Using Universal ID to Estimate Original
Sample Quantity in Short Read Detection

When the synthesized "barcode" strand is allowed to progress further into the modified sample addiitonal information may be provided by the new barcode. If the sample DNA is processed so that all Original Sample Fragments have a unique, random, universal ID (Z) ligated onto their terminal ends along with a stop position (X, missing a $5^{th}$ nucleotide in extension), primer site (a), barcode site (w), and Universal Primer site (y), then the Universal ID may be used to determine all barcodes generated from the same original fragment. If multiple barcodes are created from one sample strand then the inclusion of a Universal ID read in the barcode would allow the user to track all original sample fragments and determine the starting amount of molecules more accurately.

FIG. 20

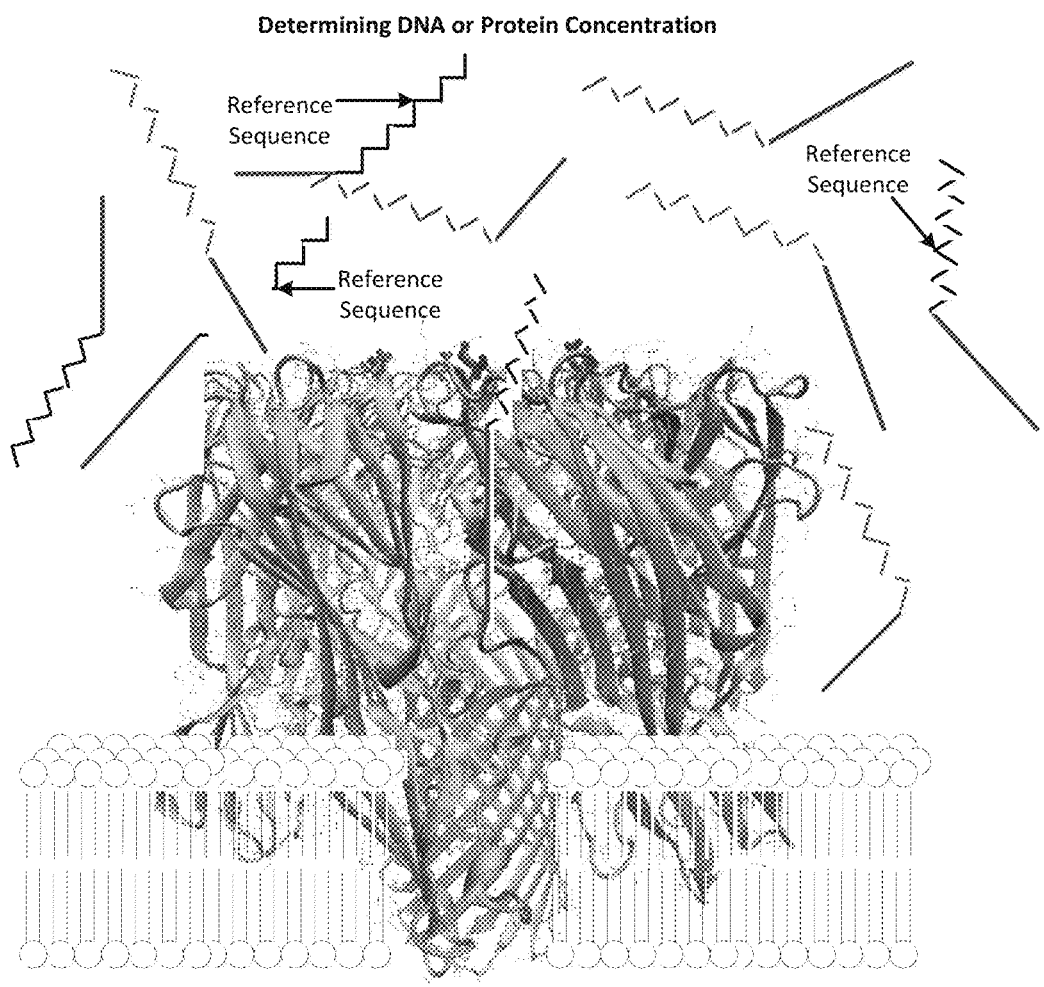

Any molecule that is barcoded will be detected in the nanopore array. A known concentration of a specific length, barcoded, reference fragment can be spiked into the mix. The relative capture rates and total captures of all components can be determined and compared to the known reference concentration to estimate concentrations. Alternately, if the system provides repeatable measurements, then a set of standard curves of capture rates for different size barcode fragments can be established and used to estimate barcode, and by extension, original sample concentrations. Any spike in for this purpose may need to include a small collection of different sized reference barcodes to account for differences in diffusion rates.

MOLECULAR DETECTION AND COUNTING USING NANOPORES

CROSS-REFERENCE TO RELATED APPLICATIONS

This application is a continuation of International Application Serial No. PCT/EP2017/076152, filed on Oct. 13, 2017, which claims the benefit of U.S. Provisional Application Ser. No. 62/407,986, filed on Oct. 13, 2016, each of which is incorporated in its entirety by this reference.

SEQUENCE LISTING INCORPORATION BY REFERENCE

This application hereby incorporates-by-reference a sequence listing submitted herewith in a computer-readable format having a file name of 33907_US1_seqlist_st25, created on Apr. 12, 2019, which is 3,930 bytes in size.

BACKGROUND OF THE INVENTION

Numerous methods for using nanopores to detect nucleic acids (e.g., DNA) or other molecules are known in the art. One common method involves applying an electric field across the nanopore to induce the nucleic acid to enter and partially block the nanopore, and measuring the current level and duration of the current blockage as the molecule rapidly translocates through the pore. Both the current level and the duration of the blockage can reveal information about the molecule (typically, a polymeric molecule such as DNA). This type of nanopore detection method has also been carried out using polymeric polyethylene glycol (PEG) molecules and the length was of the polymer was found to affect both the current level and dwell time. See e.g., Joseph W. F. Robertson, Claudio G. Rodrigues, Vincent M. Stanford, Kenneth A. Rubinson, Oleg V. Krasilnikov, and John J. Kasianowicz, *Proc. Nat'l. Acad. Sci. USA,* 104; 8207 (2007).

Single-molecule sequencing-by-synthesis (SBS) techniques using nanopore detection have been developed. See e.g., US Pat. Publ. Nos. 2013/0244340 A1, 2013/0264207 A1, 2014/0134616 A1. Kumar et al., (2012) "PEG-Labeled Nucleotides and Nanopore Detection for Single Molecule DNA Sequencing by Synthesis," Scientific Reports, 2:684; DOI: 10.1038/srep00684, as well as US Patent Application Publications US 2013/0244340 A1, published Sep. 19, 2013, US 2013/0264207 A1, published Oct. 10, 2013, and US 2014/0134616 A1, published May 14, 2014.

There remains a need for improved systems that for the detection and counting of markers or reporters of the presence of biological molecules quickly and inexpensively. Detecting and counting molecules of interest is the basis of a wide variety of analytical and diagnostic tests, including clinical diagnostics for infectious diseases, cancer, chromosomal abnormalities, and immune dysfunction; environmental testing for contaminants and infectious agents; and analytical assays for research.

SUMMARY OF THE INVENTION

The present disclosure is based, at least in part, on the use of modified nucleotide polymers capable of acting as nanopore detectable barcodes. The disclosed nanopore detectable modified nucleotide polymers, also referred to herein as nanopore detectable barcodes, are useful in a wide variety of methods for detecting and quantitating nucleic acid molecules, polypeptides, and other analytes.

In one embodiment, the present disclosure provides a method for detecting and/or quantifying a target nucleic acid molecule, the method comprising: contacting the target nucleic acid molecule with at least one primer that specifically hybridizes to the target nucleic acid molecule, resulting in a target nucleic acid molecule-primer complex; extending the primer using modified nucleotides, wherein the modified nucleotides comprise barcode units, to produce a target-modified nucleotide polymer complex; isolating the modified nucleotide polymer; detecting and/or quantifying the modified nucleotide polymer using a nanopore.

In some embodiments, the target nucleic acid molecule is selected from the group consisting of mRNA or cDNA and the primer may comprise oligo-dT. In another embodiment, the nucleic acid molecule is DNA. In some embodiments, the nucleic acid molecule is amplified.

In another embodiment, provided is a method for detecting and/or quantifying a target nucleic acid molecule, the method comprising: contacting the target nucleic acid molecule with at least a first primer and a second primer, wherein: each primer comprises a target-specific region and a universal priming site; the second primer comprises barcode coding region disposed between its target-specific region and its universal priming site; amplifying the target nucleic acid molecule to produce amplicons; isolating and denaturing the amplicons to produce single-stranded amplicons; contacting the single-stranded amplicons with the second primer; extending the second primer using a modified nucleotides to produce an amplicon-modified nucleotide polymer complex; isolating modified nucleotide polymer; detecting and/or quantifying the modified nucleotide polymer using a nanopore.

In another embodiment, provided is a multiplexed method for detecting and/or quantitating nucleic acid target molecules in a sample, comprising the steps of: contacting sample with a set of at least two oligonucleotide primers, wherein at least one primer in each set comprises a barcode template, wherein each primer comprises a universal priming sequence, and wherein the oligonucleotide primers hybridize at adjacent sites on the target nucleic acid molecules; ligating the primers; amplifying the ligated nucleic acid molecules; extending the second primer using a modified nucleotides to produce an amplicon-modified nucleotide polymer complex; isolating modified nucleotide polymer; detecting and/or quantifying the modified nucleotide polymer using a nanopore. In some embodiments, the barcode template comprises a sample index, a locus index, or a strand index.

In another embodiment, provided is a method of detecting an analyte in a sample, comprising the steps of: contacting the sample with a specific binding protein (e.g. an antibody) comprising a nanopore detectable barcode to produce an analyte-binding protein complex; isolating the analyte-binding protein complex; detecting the nanopore detectable barcode using a nanopore. In one embodiment, the nanopore-detectable barcode is attached to the specific binding protein using click chemistry.

BRIEF DESCRIPTION OF THE DRAWINGS

FIG. 1A depicts an XYZ barcode (bottom nucleotide polymer strand set forth as SEQ ID NO:1); FIG. 1B depicts a WYZ barcode (bottom nucleotide polymer strand set forth as SEQ ID NO:2); and FIG. 1C depicts a WXZ barcode (bottom nucleotide polymer strand set forth as SEQ ID NO:3). FIG. 1D sets forth a reporter key for the XYZ, WYZ, and WXZ barcodes, wherein W=Pyrrolidine (tag current level~35% O.C); X=dTmp (dT-methyl phosphonate) (tag current level~25% O.C.); Y=dT (tag current level~43%); and Z=SpC3 (propyl spacer) (tag current level~53%).

FIG. 2 depicts (FIG. 2A) the predicted nanopore-detectable current levels for the XYZ barcode; and (FIG. 2B) the measured nanopore current levels in the presence of the modified nucleotide polymer corresponding to the XYZ barcode.

FIG. 3 depicts (FIG. 3A) the predicted nanopore-detectable current levels for the WYZ barcode; and (FIG. 3B) the measured nanopore current levels in the presence of the modified nucleotide polymer corresponding to the WYZ barcode.

FIG. 4 depicts (FIG. 4A) the predicted nanopore-detectable current levels for the WXZ barcode; and (FIG. 4B) the measured nanopore current levels in the presence of the modified nucleotide polymer corresponding to the WXZ barcode.

FIGS. 5A-5E depict the use of nanopore-detectable barcodes to detect and count target molecules after a ligation-amplification reaction.

FIG. 7 depicts the use of nanopore-detectable barcodes using the primer sequence as the unique barcode template for PCR.

FIG. 8 depicts the initiation of a unique barcode read by a universal primer.

FIG. 11 depicts PCR detection with a pre-made barcode attached to a primer.

FIG. 12 depicts mRNA expression analysis using nanopore-detectable barcodes, with a direct read into the 3' UTR.

FIG. 15 depicts expression analysis using nanopore-detectable barcodes, with a read bridging over exon-intron borders.

FIG. 19 depicts the use of universal ID to estimate the number of original sample copies of a target nucleic acid molecule.

FIG. 20 depicts the measurement of sample concentration with a nanopore via spiking the sample with standard comprising a known concentration of barcoded, similarly-sized nucleic acid molecules.

DETAILED DESCRIPTION OF THE INVENTION

Relevant Definitions

Figure 1:
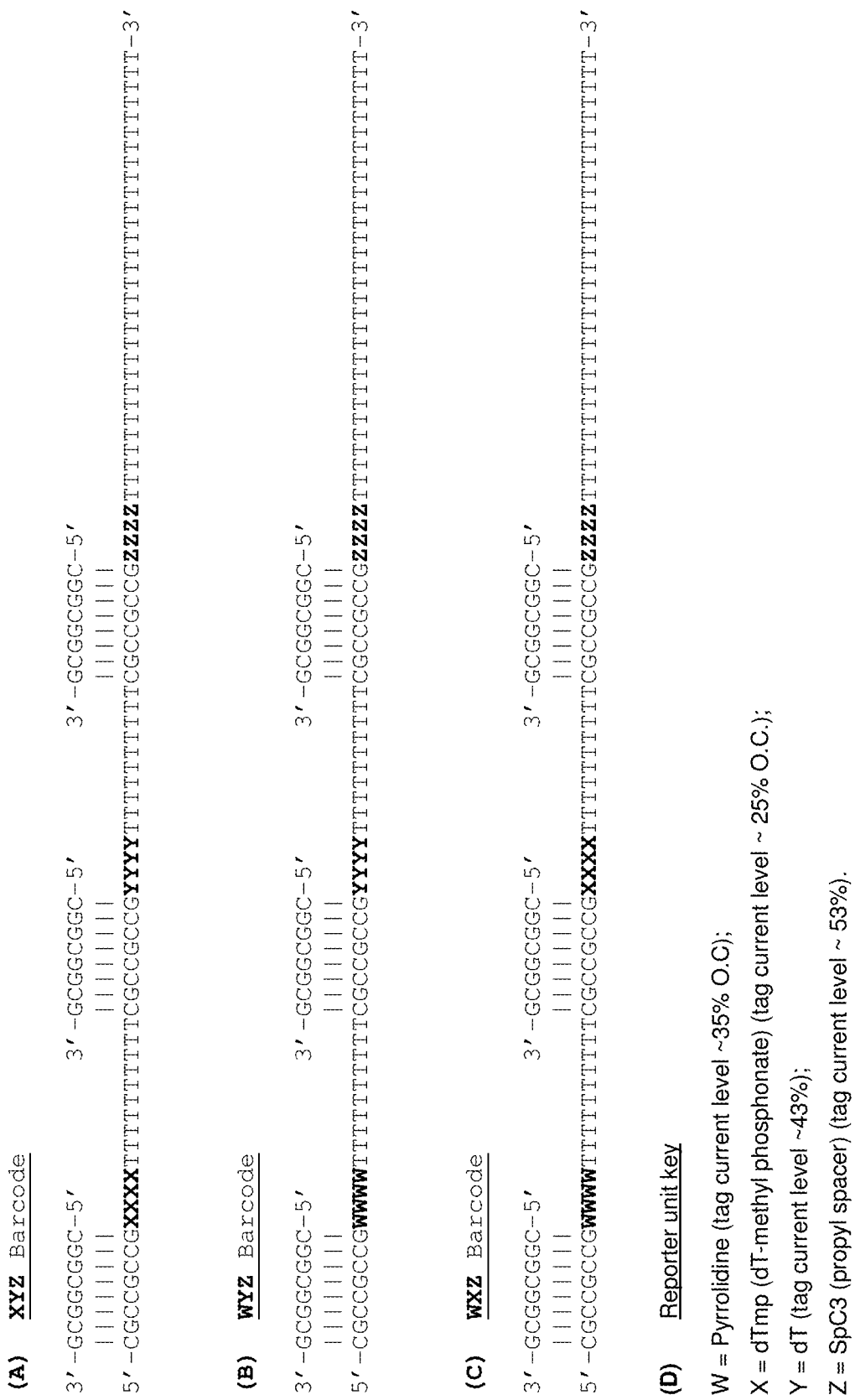
FIG. 1 depicts three specific modified nucleotide polymers, each of which includes 3 barcode units, used in the nanopore-based barcode detection experiment of Example 2.

The technical and scientific terms used in the descriptions herein will have the meanings commonly understood by one of ordinary skill in the art, unless specifically defined otherwise. Accordingly, the following terms are intended to have the following meanings.

"Nucleoside," as used herein, refers to a molecule that comprises a nucleobase attached to a sugar moiety (e.g., ribose or deoxyribose). The nucleobase can be a naturally-occurring canonical nucleobase (e.g., adenine (A), cytosine (C), guanine (G), thymine (T), or uracil (U)), a naturally-occurring modified nucleobase (e.g., 5-methyl cytosine, 5-hydroxymethyl-cytosine, 5,6-dihydrouracil, inosine, xanthine, hypoxanthine, 7-methyl guanine), or a non-naturally occurring nucleobase analog (e.g., 7-deaza-adenine, 8-bromo-guanosine, 5-formyl-cytosine, 4-thio-thymidine, O4-triazolyl-uridine, 2,6-diamino-purine).

"Nucleotide," as used herein refers to a nucleoside-5'-oligophosphate compound with three components, a 5-carbon sugar, a phosphate group, and a naturally occurring nucleobase, which is capable of acting as a substrate or an inhibitor of a nucleic acid polymerase. For example, nucleotides include but are not limited to the naturally occurring deoxyribonucleoside-5'-triphosphates, dATP, dCTP, dGTP, dTTP, and dUTP.

"Nucleotide analog," as used herein refers to a structural analog of a nucleotide, wherein one or more of the three nucleotide structure components (i.e., 5-carbon sugar, phosphate group, or nucleobase) is altered and/or not present. Nucleotide analogs include any monomer unit that can be inserted synthetically in a nucleotide polymer using amidite coupling chemistry. Exemplary nucleotide analogs can include deoxyribonucleoside-5'-triphosphate compounds which have a nucleobase analog (e.g., 7-deaza-adenosine-5'-triphosphate), or monomer unit "spacers" which lack a nucleobase (e.g., "idSp," "SpC3," etc.) but which can be inserted in a nucleotide polymer via amidite coupling chemistry.

"Nucleic acid," as used herein, refers to a polymer of nucleotide and/or nucleotide analog monomer units. Nucleic acids are also referred to herein as nucleotide polymer, modified nucleotide polymers, polynucleotides, or oligonucleotides, and include DNA and RNA, and single-, double-, triple-, and multi-stranded forms.

"Modified nucleotide polymer," as used herein refers to a polymer of nucleotides and/or nucleotide analogs that includes two or more bulky structures each adjacent to a reporter unit sequence, and optionally, one or more spacer units.

"Reporter unit" as used herein refers to a portion of a modified nucleotide polymer that includes from 4 to 10 nucleotides or from 4 to 25 nucleotide analogs (or other monomer units) and produces a detectable current level and/or dwell time upon entering, residing in, and/or translocating a nanopore under an applied voltage potential. For example, a reporter unit can include a sequence of 4 nucleotide analog monomer units, which have been inserted in a nucleotide polymer chain via phosphoramidite coupling chemistry.

"Bulky structure" as used herein refers to a moiety having a structure that is unable to pass through a nanopore. The inability of the bulky structure to pass through a nanopore can be permanent or it can be a transient, wherein the bulky structure is capable of transforming into a non-bulky structure capable of passing through the pore. For example, a bulky structure can include a double-stranded region or hairpin-forming sequence of a nucleic acid that can undergo "melting" to form a single-stranded structure that then is able to pass through the pore.

"Hairpin-forming sequence" as used herein refers to a self-complementary region of nucleic acid comprising two sequences capable of hybridizing with each other separated by a sequence of at least 4 nucleotides that is not self-complementary.

"Nanopore," as used herein, refers to a pore, channel, or passage formed or otherwise provided in a membrane or other barrier material that has a characteristic width or diameter of about 1 angstrom to about 10,000 angstroms. A nanopore can be made of a naturally-occurring pore-forming protein, such as α-hemolysin from S. aureus, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Nanopore-detectable" as used herein refers to the ability to enter into, become positioned in, be captured by, translocate through, and/or traverse a nanopore and thereby result in a detectable change in current through the nanopore.

"Nanopore-detectable barcode" or "Nanopore-detectable modified nucleotide polymer" as used interchangeably herein, refers to a complete structure of Formula (1), which is cable of being positioned in, captured by, translocated through, and/or traverse a nanopore and thereby result in a detectable change in current through the nanopore.

"Open channel current," "O.C. current," or "Background current" as used herein refers to the current level measured across a nanopore when a potential is applied and the nanopore is open (e.g., no tag is present in the nanopore).

"Reporter unit current" as used herein refers to the distinctive current level measured across a nanopore when a potential is applied and a reporter unit is present in the nanopore. Typically, the presence of a reporter unit in a nanopore alters the ion flow through the nanopore thereby altering the measured current level across the nanopore either below or above the O.C. current.

"Dwell time" as used herein in the context of capture of a reporter unit in a nanopore refers to the time that the tag spends in the nanopore as detected by a reporter unit current.

Modified Nucleotide Polymers Comprising Distinguishable Barcode Units

The various nanopore-based barcoding methods disclosed herein utilize compounds and compositions comprising modified nucleotide polymers capable of providing a series of nanopore-detectable signals upon being captured by and/or translocating a nanopore under an applied potential. This series of nanopore-detectable signals corresponds to the unique barcode associated with the modified nucleotide polymer. The structures of the modified nucleotide polymers are capable of generating distinct, measurable nanopore-detectable signals (e.g., changes in ion flow through the nanopore measured as changes in nanopore current levels relative to a baseline) based on the type, number, charge, and location of bulky structures (B), reporter units (R), and spacer units (X), which together form discrete "barcode units" in the polymer.

Briefly, and without intending to be limited by any specific molecular mechanism, the modified nucleotide polymer translocates through a nanopore under a potential, until the bulky structure (B) of the first of the polymer stops the translocation process, at least transiently. Due to the design of the modified nucleotide polymer, upon the bulky structure (B) stopping translocation, the reporter unit (R) also stops in the barrel of the nanopore, where its presence alters the ion flow through nanopore, and thereby causes a detectable change in current measured across the nanopore. The design of the bulky structure (B) allows it to pass through the nanopore after some period time (e.g., upon melting of a duplex or hairpin associated with the bulky structure), thereby permitting the modified nucleotide polymer to translocate through the nanopore until the bulky structure (B) in the next in the series of barcode units reaches the lumen of the pore and stops, thereby placing the next reporter unit (R) in the barrel of the nanopore. The distance between the adjacent bulky structures can be modified by the length of the spacer unit (X) portion of each barcode unit. This process of momentary bulky structure stoppage with associated reporter unit (R) signal detection continues until the whole modified nucleotide polymer has translocated the nanopore, at which point the ion flow through and detectable current level across the nanopore returns to the open channel (O.C.) level. Thus, the series of the reporter unit signals detected between two O.C. level signals represents the barcode read from the series of barcode units of the modified nucleotide polymer.

As described herein, the compounds comprising modified nucleotide polymers of the present disclosure can be prepared with 3, 4, 5, 6, 7, 8, or more barcode units, which will allow for tens of thousands of unique nanopore detectable barcodes. Because of the standard polymer structure of the modified nucleotide polymers comprising barcode units disclosed herein, the ordinary artisan can easily adapt them for a wide range of uses involving nanopore detection systems. Accordingly, it is contemplated that the modified nucleotide polymers disclosed herein can be incorporated into any of the nanopore-based methods for detecting analytes disclosed.

Accordingly, in one embodiment the present disclosure provides a compound comprising a modified nucleotide polymer of structural formula (I):

$$[(B)-(R^i)-(X)]_n-(Y) \qquad (I)$$

wherein, B is a bulky structure; R is a reporter unit, and the superscript i is the reporter unit identifier; X is a spacer unit, and the portion of the polymer comprising B, R, and X, is a barcode unit; n is the number of barcode units, and n is from 2 to 8; and Y is a tail unit comprising 20 to 100 monomer units.

In order to better distinguish the different barcode units of the modified nucleotide polymer when it is captured by and/or translocates through a nanopore, the modified nucleotide polymers are designed such that the adjacent reporter units provide distinguishable nanopore detectable signals. Accordingly, in some embodiments, the reporter units of adjacent barcode units are different and thereby provide distinguishable nanopore detectable signals. For example, the reporter units of adjacent barcode units are selected to produce different, distinguishable reporter unit current levels and/or dwell times when they are captured by and/or translocate through the nanopore. The design of distinguishable reporter units comprising nucleotides and/or nucleotide analog monomer units is disclosed in the Examples and elsewhere herein.

Accordingly, in some embodiments, the compound of formula (I) has 3 barcode units (i.e., n=3), and comprises a modified nucleotide polymer represented by structural formula (Ia)

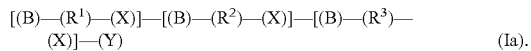

In order to provide distinguishable nanopore detectable signals associated with the 3 barcode units, the reporter units can be selected such that any 2 adjacent barcode units comprise reporter units are different such and provide different distinguishable nanopore detectable signals. For example, $R^1$ is different than $R^2$, and $R^3$ is different than $R^2$. However, the reporter units of non-adjacent barcode units can be the same, e.g., $R^1=R^3$, and still provide distinguishable nanopore detectable signals due to the intervening barcode unit providing a different detectable signal. Of course, it is also contemplated that, a modified nucleotide polymer can comprise barcode units, each having a different reporter unit (e.g., $R^1$, $R^2$, and $R^3$ all different), thereby allowing the signal from each barcode unit to be distinguished by a nanopore detection system. Further specific disclosure of the design and nanopore detection of exemplary compounds comprising modified nucleotide polymers with 3 distinguishable barcode units is provided in the Examples.

The compound of structural formula (Ia) provides 3 barcode units, which theoretically allows 27 (i.e., $3^3$) different barcode unit combinations. However, if the compound is further designed such that any 2 adjacent barcode units comprise different reporter units, then the total number of possible barcodes provided by this modified nucleotide polymer having 3 barcode units is only 12. Thus, it is contemplated that the methods of the present disclosure can be carried using compounds comprising modified nucleotide polymers comprising not only 3, but also 4, 5, 6, 7, 8, or more barcode units, and optionally wherein any 2 adjacent barcode units of the polymer have different reporter units.

Accordingly, in some embodiments, the compound of formula (I) has n=4, and comprises a modified nucleotide polymer represented by structural formula (Ib)

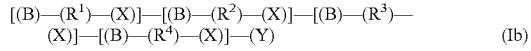

optionally, wherein any 2 adjacent barcode units of the polymer have different reporter units wherein the polymer comprises 4 different barcode units. Optionally, in some embodiments, each barcode unit has a different reporter unit, $R^1$, $R^2$, $R^3$, or $R^4$ and each of the reporter units provides a nanopore detectable signal that is different and distinguishable from the other reporter units.

In some embodiments, the compound of formula (I) has n=5, and comprises a modified nucleotide polymer represented by structural formula (Ic)

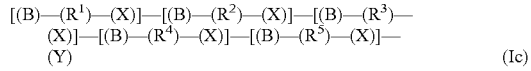

optionally, wherein any 2 adjacent barcode units of the polymer have different reporter units wherein the polymer comprises 4 different barcode units. Optionally, in some embodiments, each barcode unit has a different reporter unit, $R^1$, $R^2$, $R^3$, $R^4$, or $R^5$ and each of the reporter units provides a nanopore detectable signal that is different and distinguishable from the other reporter units.

In some embodiments, the compound of formula (I) has n=6, and comprises a modified nucleotide polymer represented by structural formula (Id)

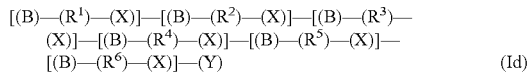

optionally, wherein any 2 adjacent barcode units of the polymer have different reporter units wherein the polymer comprises 4 different barcode units. Optionally, in some embodiments, each barcode unit has a different reporter unit, $R^1$, $R^2$, $R^3$, $R^4$, $R^5$, or $R^6$ and each of the reporter units provides a nanopore detectable signal that is different and distinguishable from the other reporter units.

Compounds Comprising Multiple Modified Nucleotide Polymers and Additional Analyte Associating Features Generally, the methods of the present disclosure detect and/or quantify an "analyte" using a compound that specifically associates with an analyte and further comprises a modified nucleotide polymer of structural formula (I), which is capable of generating a nanopore detectable barcode. It is contemplated that such compounds for use in the disclosed methods can include one or more modified nucleotide polymers of formula (I) depending on the specific method of use. Additionally, such compounds comprising one or more modified nucleotide polymers of structural formula (I) can further comprise other structural features useful for associating the compound with the desired analyte. For example, such "affinity binding" or "probe" features can include specific nucleotide sequences that specifically hybridize (or otherwise specifically bind) to an analyte nucleic acid sequence of interest. For example, in some embodiments, the present disclosure contemplates a compound comprising a "probe" nucleotide polymer sequence and a modified nucleotide polymer of structural formula (I), wherein the "probe" nucleotide polymer sequence is capable of specifically associating the compound with a target analyte, and the modified nucleotide polymer is capable of generating a nanopore-detectable barcode.

In another embodiment, the variety of available reporter unit structures can provide for a wide range of modified nucleotide polymer structures, each having a different sequence of barcode units, and thus each having specific, distinguishable signatures for nanopore detection. For example, based on the methods described herein, one of skill in the art can identify sets of modified nucleotide polymers that exhibit readily distinguishable blocking current levels. Such a set could be used in a wide variety of methods of detecting and/or quantifying analytes disclosed herein to perform assays allowing simultaneous detection and/or quantification of hundreds or even thousands of different analytes using a nanopore detection system.

Bulky Structures (B)

The compounds comprising modified nucleotide polymers of the present disclosure comprise a series of barcode units, each comprising a bulky structure (B) that, at least transiently, cannot pass through a nanopore. Each bulky structure stops the modified nucleotide polymer from completely threading (i.e., translocating) through the nanopore for some period of time and effectively positions the adjacent reporter unit (R) in the barrel of the nanopore for optimal signal measurement. Thus, each of the series of barcode units comprising a bulky structure is captured transiently in the nanopore and during that time each of the series of associated reporter units produces a detectable change in ion flow through the pore that results in reporter unit currents and/or associated dwell times that allow it to be identified and/or counted (i.e., quantified).

Generally, the bulky structure comprises a molecular moiety having an approximate size or diameter of 2 nm diameter (i.e., the nanopore diameter) and which can be attached to a nucleotide polymer. Such bulky structures typically have at least two dimensions that are greater than ~2 nm. Furthermore, in the embodiments of the present disclosure, the bulky structure exists only transiently, and is capable after a certain time period and/or application of certain conditions (e.g., temperature, salt concentration, applied voltage and/or electrophoretic force) of effectively disappearing or changing in size such that it can pass through the nanopore. In some embodiments, the bulky structure is a double-stranded nucleic acid structure that is capable of transforming into a non-bulky structure that can pass through the nanopore by melting to a single strand. Examples of bulky structures that can undergo such a transformation include but are not limited to double-stranded nucleic acid structures, nucleic acid hairpin structures, multi-hairpin nucleic acid structures, multi-arm nucleic acid structures, triplex DNA, and G quartet quadruplex DNA. U.S. Pat. No. 8,845,880 B2, which is hereby incorporated by reference herein, provides further description and examples of bulky structures and their use in the context of nanopore detection.

Double-Stranded Sequences as Bulky Structures

In some embodiments, the modified nucleotide polymers of the present disclosure comprise a bulky structure (B), wherein the bulky structure comprises a double-stranded (or duplex) sequence region. A double-stranded region is structurally small enough to enter the vestibule of an α-HL nanopore but too large to enter the barrel of the nanopore because the constriction at the top of the barrel is too small (1.5 nm) for double-stranded region (~2 nm). Thus, a double-stranded region adjacent to a reporter unit effectively allows the reporter unit to become threaded into (or captured by) the barrel of the nanopore without completely translocating (i.e., passing through). Upon capture, the ion flow through the nanopore is altered by the presence of the reporter unit in the barrel resulting in an altered characteristic current level (i.e., reporter unit current). With sufficient applied voltage and time, however, the duplex region melts forming a single-stranded structure that is capable of translocating the nanopore, either completely or until the next in the series of bulky structures reaches the nanopore constriction site.

The ability of single-stranded regions of nucleic acids to form duplex structures is well understood by the ordinary artisan in the art of nucleic acid hybridization and detection. Generally, any a complementary oligonucleotide sequence can be easily prepared and conditioned determined under which that oligonucleotide will form a double-stranded region with its complementary sequence that is part of a longer nucleotide polymer. In the context of the particular nanopore detection methods of the present disclosure that a wide range of double-stranded structures can be used as bulky structures in the modified nucleotide polymers of the present disclosure.

It is contemplated that the length and/or nucleotide composition of the double-strand forming sequence used as a bulky structure can be selected for particular nanopore detection conditions such that it maintains the double-stranded structure does not pass through the nanopore for a time sufficient to optimally detect the distinctive current level and/or dwell time of the adjacent reporter unit. In some embodiments, the bulky structure comprises an oligonucleotide sequence region, of 5-mer, 6-mer, 7-mer, 8-mer, 9-mer, adjacent to the reporter unit that forms a duplex with a complementary oligonucleotide of 5-mer, 6-mer, 7-mer, 8-mer, 9-mer. Exemplary double-stranded bulky structures are also described in the Examples herein.

It is also contemplated, that the modified nucleotide polymers of the present disclosure comprise a bulky structure (B), wherein the bulky structure is a double-stranded region formed by a hairpin-forming (HP) sequence. In one embodiment, the present disclosure provides the above-described compound comprising a modified nucleotide polymer of formula (I), wherein at least one of the bulky structures (B) is a hairpin structure. A wide variety of hairpin-forming sequences (HP) capable of forming structures are available and well-known to the ordinary artisan. In one embodiment, the hairpin-forming sequence (HP) comprises two 7-mer sequences that are capable of hybridizing with each other linked by a 4-mer non-complementary sequence. In one embodiment, the two 7-mer sequences are: GCGGCGC and GCGCCGC, and in one embodiment, the hairpin-forming sequence consists of the 18-mer sequence GCGGCGCGTAAGCGCCGC (SEQ ID NO:4).

In one embodiment, the present disclosure provides compounds comprising the 18-mer HP sequence 5'-GCGGCGCGTAAGCGCCGC-3' (SEQ ID NO:4). As shown in Example 1, this 18-mer HP sequence forms a bulky structure that transiently maintains its double stranded structure such that an adjacent reporter unit attached to its 3' end of the HP sequence is captured by an α-HL pore to provide a detectable reporter unit current and/or dwell time before the double-stranded region melts thereby allowing the polymer to completely translocate the nanopore.

In theory, any biological macromolecule (e.g., nucleic acids, proteins, enzymes, receptors, antibodies), that can be attached to specifically to the modified nucleotide polymer adjacent to the reporter unit, and can detach under specified conditions, can be used as a bulky structure. Exemplary biological macromolecules could include, but are not limited to: (a) an avidin or a streptavidin protein which can be attached to a modified nucleotide polymer with a terminal biotin; (b) an antibody protein (or fragment thereof) attached to the modified nucleotide polymer via an appropriate ligand (e.g., digoxigenin ligand which binds an anti-digoxigenin antibody); (c) a DNA binding protein (e.g., recA protein, transcription factors, restriction methylases, helicases and proteins derived from them) which bind to a nucleotide sequence of the modified nucleotide polymer thereby creating a bulky structure attached to the polymer; or (d) a DNA or RNA polymerase or ligase, which can bind with a nucleotide sequence of the modified nucleotide polymer sequences, thereby creating a bulky structure attached to the polymer.

Reporter Units (R)

The compounds comprising modified nucleotide polymers of the present disclosure comprise a series of barcode units, each barcode unit also comprises a reporter unit (R). The reporter unit is a portion of the modified nucleotide polymer that includes from 4 to 10 nucleotides or from 4 to 25 nucleotide analogs (or other monomer units). The reporter unit is located adjacent to the bulky structure which results in the reporter unit being positioned in the barrel of the nanopore when the bulky structure is stopped by its inability to pass through the pore. The presence of the reporter unit (R) in the barrel of the nanopore produces the unique nanopore-detectable signal (e.g., current level and/or dwell time).

Reporter units useful in the modified nucleotide polymers of the present disclosure comprise from 4 to 10 nucleotide or 4 to 25 nucleotide analog monomer units. Generally, the monomer units can be of any type inserted synthetically in a nucleotide polymer via amidite coupling chemistry. It is contemplated that reporter units of the present disclosure can comprise nucleotide monomer units and/or nucleotide analog monomer units. The nucleotide analog monomer units generally have structures with charge and steric bulk that is substantially altered relative to the naturally occurring (or canonical) nucleotide monomer units (e.g., dA, dC, dG, dT, and dU). The altered charge and size characteristics of the nucleotide analog monomer units allows for reporter units capable of producing a wider range of nanopore detectable signals (e.g., reporter unit currents and/or dwell times) relative to the four canonical nucleotide monomer units upon entering, residing, and/or passing through a nanopore that is under an applied voltage potential.

Without intending to be limited by any specific mechanism, it is believed that the reporter units of the modified nucleotide polymers are located in the polymer adjacent to the bulky structure such that the reporter unit resides in the barrel of the nanopore, and that this location provides the optimal levels of measurable alterations in the ion flow through the nanopore under a voltage potential. These alterations result in large measured reporter unit currents and/or dwell time relative to nanopore O.C. current, and are optimal for identifying the specific reporter unit and thus, the specific modified nucleotide polymer barcode unit.

The alterations in nanopore detectable measurements produced by the presence of the reporter units in the modified nucleotide polymer can include decreased or increased ion flow, and results reporter unit currents and/or dwell-times. In some embodiments, a reporter unit comprising nucleotide analog monomer units is used which results in greatly increased dwell time relative to a reporter unit comprising a naturally occurring nucleotide. Increased dwell-time is particularly advantageous for use in nanopore detection systems since it allows for more precise and accurate measurements, which further provides better and more accurate identification of the modified nucleotide polymer barcode and any associated analyte being measured. In some embodiments, the detectable dwell time produced by the reporter unit (R) is at least 2-fold, at least 4-fold, at least 5-fold, at least 8-fold, or at least 10-fold. In some embodiments, the detectable dwell time produced by the reporter unit (R) is at least 300 msec, at least 500 msec, at least 750 msec, at least 1000 msec, at least 2000 msec, or at least 5000 msec.

An important feature of the reporter units comprising nucleotide analog monomer units is the great variety of nucleotide analogs available and the ease of insertion of these structures into a modified nucleotide polymer via amidite coupling chemistry. For example, Table 1 (below) lists over 300 exemplary amidite reagents (e.g., phosphoramidite or phosphonamidite) that can be used to synthesize reporter units (R) in the modified nucleotide polymers of the present disclosure. Each of the amidite reagents listed in Table 1 is commercially available, however, there are hundreds, if not thousands, more amidite reagents having nucleotide analog structures that have been published and would be available to the skilled artisan for use in preparing reporter units in modified nucleotide polymers of the present disclosure.

TABLE 1

| Nucleotide Analog Amidite Reagents | Catalog No. |
|---|---|
| Commercially available from: Glen Research, 22825 Davis Drive, Sterling, VA, USA | |
| dA-5'-CE phosphoramidite | 10-0001 |
| dC-5'-CE phosphoramidite | 10-0101 |
| dT-5'-CE phosphoramidite | 10-0301 |
| 7-Deaza-dA-CE phosphoramidite | 10-1001 |
| N6-Me-dA-CE phosphoramidite | 10-1003 |
| 3'-dA-CE phosphoramidite | 10-1004 |
| Etheno-dA-CE phosphoramidite | 10-1006 |
| 8-Br-dA-CE phosphoramidite | 10-1007 |
| 8-oxo-dA-CE phosphoramidite | 10-1008 |
| pdC-CE phosphoramidite | 10-1014 |
| TMP-F-dU-CE phosphoramidite | 10-1016 |
| Pyrrolo-dC-CE phosphoramidite | 10-1017 |
| 5-Me-dC Brancher phosphoramidite | 10-1018 |
| Amino-Modifier C6 dC | 10-1019 |
| 7-deaza-dG-CE phosphoramidite | 10-1021 |
| 8-Br-dG-CE phosphoramidite | 10-1027 |
| 8-oxo-dG-CE phosphoramidite | 10-1028 |
| dmf-dG-CE phosphoramidite | 10-1029 |
| 5'-OMe-dT-CE phosphoramidite | 10-1031 |
| O4-Me-dT-CE phosphoramidite | 10-1032 |
| 4-Thio-dT-CE phosphoramidite | 10-1034 |
| Carboxy-dT | 10-1035 |
| 2-Thio-dT-CE phosphoramidite | 10-1036 |
| Amino-Modifier C2 dT | 10-1037 |
| Biotin-dT | 10-1038 |
| Amino-Modifier C6 dT | 10-1039 |
| dI-CE phosphoramidite | 10-1040 |
| 2'-DeoxyNebularine-CE phosphoramidite (Purine) | 10-1041 |
| O6-Phenyl-dI-CE phosphoramidite | 10-1042 |
| 5-Nitroindole-CE phosphoramidite | 10-1044 |
| 2-Aminopurine-CE phosphoramidite | 10-1046 |
| dP-CE phosphoramidite | 10-1047 |
| dK-CE phosphoramidite | 10-1048 |
| dU-CE phosphoramidite | 10-1050 |
| O4-Triazolyl-dU-CE phosphoramidite | 10-1051 |
| 4-Thio-dU-CE phosphoramidite | 10-1052 |
| 5-OH-dU-CE phosphoramidite | 10-1053 |
| pdU-CE phosphoramidite | 10-1054 |
| 2'-deoxypseudoU-CE phosphoramidite | 10-1055 |
| Fluorescein-dT phosphoramidite | 10-1056 |
| TAMRA-dT | 10-1057 |
| Dabcyl-dT | 10-1058 |
| EDTA-C2-dT-CE phosphoramidite | 10-1059 |
| 5-Me-dC-CE phosphoramidite | 10-1060 |
| 5-Me-2'-deoxyZebularine-CE phosphoramidite | 10-1061 |
| 5-Hydroxymethyl-dC-CE phosphoramidite | 10-1062 |
| 5-OH-dC-CE phosphoramidite | 10-1063 |
| 3'-dC-CE phosphoramidite | 10-1064 |
| dmf-5-Me-isodC-CE phosphoramidite | 10-1065 |
| 5-Carboxy-dC-CE phosphoramidite | 10-1066 |
| N4-Et-dC-CE phosphoramidite | 10-1068 |
| O6-Me-dG-CE phosphoramidite | 10-1070 |
| 6-thio-dG-CE phosphoramidite | 10-1072 |
| 7-Deaza-8-aza-dG-CE phosphoramidite (PPG) | 10-1073 |
| 3'-dG-CE phosphoramidite | 10-1074 |
| 7-deaza-dX-CE phosphoramidite | 10-1076 |
| dmf-isodG-CE phosphoramidite | 10-1078 |
| 8-Amino-dG-CE phosphoramidite | 10-1079 |
| 5-Br-dC-CE phosphoramidite | 10-1080 |
| 5-I-dC-CE phosphoramidite | 10-1081 |
| 2-F-dI-CE phosphoramidite | 10-1082 |
| 7-deaza-8-aza-dA-CE phosphoramidite | 10-1083 |
| 3'-dT-CE phosphoramidite | 10-1084 |
| 2-Amino-dA-CE phosphoramidite | 10-1085 |
| 8-Amino-dA-CE phosphoramidite | 10-1086 |
| 3-deaza-dA-CE phosphoramidite | 10-1088 |
| Amino-Modifier C6 dA | 10-1089 |
| 5-Br-dU-CE phosphoramidite | 10-1090 |
| 5-I-dU-CE phosphoramidite | 10-1091 |
| 5-F-dU-CE phosphoramidite | 10-1092 |
| 5-Hydroxymethyl-dU-CE phosphoramidite | 10-1093 |
| Thymidine Glycol CE phosphoramidite | 10-1096 |
| AP-dC-CE phosphoramidite | 10-1097 |
| 8,5'-Cyclo-dA CE phosphoramidite | 10-1098 |
| dA-Me phosphonamidite | 10-1100 |

TABLE 1-continued

| Nucleotide Analog Amidite Reagents | Catalog No. |
|---|---|
| Ac-dC-Me phosphonamidite | 10-1115 |
| dG-Me phosphonamidite | 10-1120 |
| dT-Me phosphonamidite | 10-1130 |
| dA-PACE phosphoramidite | 10-1140 |
| Ac-dC-PACE phosphoramidite | 10-1150 |
| dG-PACE phosphoramidite | 10-1160 |
| dT-PACE phosphoramidite | 10-1170 |
| dA-H-Phosphonate, TEA Salt | 10-1200 |
| dC-H-Phosphonate, DBU Salt | 10-1210 |
| dG-H-Phosphonate, TEA Salt | 10-1220 |
| dT-H-Phosphonate, TEA Salt | 10-1230 |
| Pac-dA-Me phosphoramidite | 10-1301 |
| Ac-dC-Me phosphoramidite | 10-1315 |
| iPr-Pac-dG-Me phosphoramidite | 10-1321 |
| dT-Me phosphoramidite | 10-1330 |
| CleanAmp™-Pac-dA-CE phosphoramidite | 10-1440 |
| CleanAmp™-Ac-dC-CE phosphoramidite | 10-1450 |
| CleanAmp™-Pac-dG-CE phosphoramidite | 10-1460 |
| CleanAmp™-dT-CE phosphoramidite | 10-1470 |
| 1-Me-dA-CE phosphoramidite | 10-1501 |
| N6-Ac-N6-Me-dA-CE phosphoramidite | 10-1503 |
| 5-Hydroxymethyl-dC II-CE phosphoramidite | 10-1510 |
| 5-aza-5,6-dihydro-dC-CE phosphoramidite | 10-1511 |
| N4-Ac-N4-Et-dC-CE phosphoramidite | 10-1513 |
| 5-Formyl-dC-CE phosphoramidite | 10-1514 |
| tC-CE phosphoramidite | 10-1516 |
| tC°-CE phosphoramidite | 10-1517 |
| tC-nitro-CE phosphoramidite | 10-1518 |
| 8-D-dG-CE phosphoramidite | 10-1520 |
| dDs-CE phosphoramidite | 10-1521 |
| Pac-ds-CE phosphoramidite | 10-1522 |
| dPa-CE phosphoramidite | 10-1523 |
| dDss-CE phosphoramidite | 10-1524 |
| N2-Amino-Modifier C6 dG | 10-1529 |
| 5,6-Dihydro-dT-CE phosphoramidite | 10-1530 |
| N3-Cyanoethyl-dT | 10-1531 |
| 5'-Dabsyl-dT-CE phosphoramidite | 10-1532 |
| N-POM Caged-dT-CE phosphoramidite | 10-1534 |
| NHS-Carboxy-dT | 10-1535 |
| Fmoc Amino-Modifier C6 dT | 10-1536 |
| dX-CE phosphoramidite | 10-1537 |
| S-Bz-Thiol-Modifier C6-dT | 10-1538 |
| DBCO-dT-CE phosphoramidite | 10-1539 |
| C8-Alkyne-dT-CE phosphoramidite | 10-1540 |
| C8-TIPS-Alkyne-dC-CE phosphoramidite | 10-1541 |
| C8-TMS-Alkyne-dC-CE phosphoramidite | 10-1542 |
| C8-Alkyne-dC-CE phosphoramidite | 10-1543 |
| C8-TIPS-Alkyne-dT-CE phosphoramidite | 10-1544 |
| C8-TMS-Alkyne-dT-CE phosphoramidite | 10-1545 |
| 5,6-Dihydro-dU-CE phosphoramidite | 10-1550 |
| 5-Ethynyl-dU-CE phosphoramidite | 10-1554 |
| Ac-5-Me-dC-CE phosphoramidite | 10-1560 |
| 5-Formyl dC III CE phosphoramidite | 10-1564 |
| Ferrocene-dT-CE phosphoramidite | 10-1576 |
| Pyrene-dU-CE phosphoramidite | 10-1590 |
| Perylene-dU-CE phosphoramidite | 10-1591 |
| 8,5'-Cyclo-dG-CE phosphoramidite | 10-1598 |
| Pac-dA-CE phosphoramidite | 10-1601 |
| iPr-Pac-dG-CE phosphoramidite | 10-1621 |
| dA-Thiophosphoramidite | 10-1700 |
| dC-Thiophosphoramidite | 10-1710 |
| dG-Thiophosphoramidite | 10-1720 |
| dT-Thiophosphoramidite | 10-1730 |
| Chemical Phosphorylation Reagent | 10-1900 |
| Chemical Phosphorylation Reagent II | 10-1901 |
| Solid Chemical Phosphorylation Reagent II | 10-1902 |
| 5'-Amino-Modifier 5 | 10-1905 |
| 5'-Amino-Modifier C6 | 10-1906 |
| 5'-DMS(O)MT-Amino-Modifier C6 | 10-1907 |
| 5'-Hexynyl phosphoramidite | 10-1908 |
| Spacer phosphoramidite 9 | 10-1909 |
| 5'-Amino-Modifier C12 | 10-1912 |
| Spacer phosphoramidite C3 | 10-1913 |
| Pyrrolidine-CE phosphoramidite | 10-1915 |
| 5'-Amino-Modifier C6-TFA | 10-1916 |
| 5'-Amino-Modifier TEG CE-phosphoramidite | 10-1917 |
| Spacer phosphoramidite 18 | 10-1918 |
| 5'-Aminooxy-Modifier-11-CE phosphoramidite | 10-1919 |
| Symmetric Doubler phosphoramidite | 10-1920 |
| Trebler phosphoramidite | 10-1922 |
| 5'-Amino-Modifier C3-TFA | 10-1923 |
| Long Trebler phosphoramidite | 10-1925 |
| 5'-Thiol-Modifier C6 | 10-1926 |
| Abasic II phosphoramidite | 10-1927 |
| Spacer C12 CE phosphoramidite | 10-1928 |
| 5'-I-dT-CE phosphoramidite | 10-1931 |
| 5'-Amino-dT-CE phosphoramidite | 10-1932 |
| 5'-Aldehyde-Modifier C2 phosphoramidite | 10-1933 |
| 5-Formylindole-CE phosphoramidite | 10-1934 |
| 5'-Carboxy-Modifier C10 | 10-1935 |
| Thiol-Modifier C6 S-S | 10-1936 |
| Thiol-Modifier C6 S-S | 10-1936 |
| 5'-Maleimide-Modifier phosphoramidite | 10-1938 |
| Spermine phosphoramidite | 10-1939 |
| 5'-DBCO-TEG phosphoramidite | 10-1941 |
| 5'-Carboxy-Modifier C5 | 10-1945 |
| 5'-Bromohexyl phosphoramidite | 10-1946 |
| 5'-Amino-Modifier C6-PDA | 10-1947 |
| 5'-Amino-Modifier C12-PDA | 10-1948 |
| 5'-Amino-Modifier TEG PDA | 10-1949 |
| DesthiobiotinTEG phosphoramidite | 10-1952 |
| Biotin phosphoramidite | 10-1953 |
| BiotinTEG phosphoramidite | 10-1955 |
| Fluorescein phosphoramidite | 10-1963 |
| 6-Fluorescein phosphoramidite | 10-1964 |
| Acridine phosphoramidite | 10-1973 |
| Cholesteryl-TEG phosphoramidite | 10-1975 |
| 5'-Cholesteryl-TEG phosphoramidite | 10-1976 |
| α-Tocopherol-TEG phosphoramidite | 10-1977 |
| Stearyl phosphoramidite | 10-1979 |
| Psoralen C2 phosphoramidite | 10-1982 |
| Psoralen C6 phosphoramidite | 10-1983 |
| DNP-TEG phosphoramidite | 10-1985 |
| 5'-Trimethoxystilbene Cap phosphoramidite | 10-1986 |
| 5'-Pyrene Cap phosphoramidite | 10-1987 |
| Dithiol Serinol phosphoramidite | 10-1991 |
| Alkyne-Modifier Serinol phosphoramidite | 10-1992 |
| Protected Biotin Serinol phosphoramidite | 10-1993 |
| 6-Fluorescein Serinol phosphoramidite | 10-1994 |
| Protected BiotinLC Serinol phosphoramidite | 10-1995 |
| Amino-Modifier Serinol phosphoramidite | 10-1997 |
| Pac-A-CE phosphoramidite | 10-3000 |
| Bz-A-CE phosphoramidite | 10-3003 |
| A-TOM-CE phosphoramidite | 10-3004 |
| N6-Methyl-A-CE phosphoramidite | 10-3005 |
| Zebularine-CE phosphoramidite | 10-3011 |
| Pyridin-2-one-CE phosphoramidite | 10-3012 |
| C-TOM-CE phosphoramidite | 10-3014 |
| Ac-C-CE phosphoramidite | 10-3015 |
| Pyrrolo-C-TOM-CE phosphoramidite | 10-3017 |
| iPr-Pac-G-CE phosphoramidite | 10-3021 |
| G-TOM-CE phosphoramidite | 10-3024 |
| Ac-G-CE phosphoramidite | 10-3025 |
| U-CE phosphoramidite | 10-3030 |
| U-TOM-CE phosphoramidite | 10-3034 |
| Amino-Modifier C6-U phosphoramidite | 10-3039 |
| I-CE phosphoramidite | 10-3040 |
| 5-Me-U-CE phosphoramidite | 10-3050 |
| 4-Thio-U-TOM-CE phosphoramidite | 10-3052 |
| PseudoUridine-CE phosphoramidite | 10-3055 |
| 5-Me-C-TOM-CE phosphoramidite | 10-3064 |
| 2-Aminopurine-TBDMS-CE phosphoramidite | 10-3070 |
| 6-Thio-G-CE phosphoramidite | 10-3072 |
| 8-Aza-7-deaza-A-CE phosphoramidite | 10-3083 |
| 2,6-Diaminopurine-TOM-CE phosphoramidite | 10-3085 |
| Br-U-CE phosphoramidite | 10-3090 |
| 5-I-U-CE phosphoramidite | 10-3091 |
| 2'-OMe-A-CE phosphoramidite | 10-3100 |
| 2'-OMe-C-CE phosphoramidite | 10-3110 |
| 2'-OMe-TMP-5-F-U-CE phosphoramidite | 10-3111 |
| 2'-OMe-Ac-C-CE phosphoramidite | 10-3115 |
| 2'-OMe-3-deaza-5-aza-C-CE phosphoramidite | 10-3116 |
| 2'-OMe-ibu-G-CE phosphoramidite | 10-3120 |
| 2'-OMe-G-CE phosphoramidite | 10-3121 |
| 2'-OMe-2-Aminopurine-CE phosphoramidite | 10-3123 |
| 2'-OMe-2,6-Diaminopurine-CE phosphoramidite | 10-3124 |

TABLE 1-continued

| Nucleotide Analog Amidite Reagents | Catalog No. |
| --- | --- |
| 2'-OMe-U-CE phosphoramidite | 10-3130 |
| 2'-OMe-5-Me-U-CE phosphoramidite | 10-3131 |
| 2'-OMe-5-F-U-CE phosphoramidite | 10-3132 |
| 2'-OMe-I-CE phosphoramidite | 10-3140 |
| 2'-OMe-5-Me-C-CE phosphoramidite | 10-3160 |
| 2'-OMe-5-Br-U-CE phosphoramidite | 10-3190 |
| 2'-F-A-CE phosphoramidite | 10-3400 |
| 2'-F-Ac-C-CE phosphoramidite | 10-3415 |
| 2'-F-G-CE phosphoramidite | 10-3420 |
| 2'-F-U-CE phosphoramidite | 10-3430 |
| 1-Me-A-CE phosphoramidite | 10-3501 |
| 2'-OMe-Pac-A-CE phosphoramidite | 10-3601 |
| 2'-OMe-iPr-Pac-G-CE phosphoramidite | 10-3621 |
| 2'-F-A-ANA-CE phosphoramidite | 10-3800 |
| 2'-F-C-ANA-CE phosphoramidite | 10-3810 |
| 2'-F-Ac-C-ANA-CE phosphoramidite | 10-3815 |
| 2'-F-G-ANA-CE phosphoramidite | 10-3820 |
| 2'-F-U-ANA-CE phosphoramidite | 10-3830 |
| rSpacer CE phosphoramidite | 10-3914 |
| PC Amino-Modifier phosphoramidite | 10-4906 |
| PC Spacer phosphoramidite | 10-4913 |
| PC Linker phosphoramidite | 10-4920 |
| PC Biotin phosphoramidite | 10-4950 |
| Azobenzene phosphoramidite | 10-5800 |
| 2,2'-Dipicolylamine phosphoramidite | 10-5801 |
| 5'-Fluorescein phosphoramidite | 10-5901 |
| 5'-Hexachloro-Fluorescein phosphoramidite | 10-5902 |
| 5'-Tetrachloro-Fluorescein phosphoramidite | 10-5903 |
| SIMA (HEX) phosphoramidite | 10-5905 |
| 5'-Dichloro-dimethoxy-Fluorescein phosphoramidite II | 10-5906 |
| 5'-Dabcyl phosphoramidite | 10-5912 |
| Cyanine 3 phosphoramidite | 10-5913 |
| Cyanine 3.5 phosphoramidite | 10-5914 |
| Cyanine 5 phosphoramidite | 10-5915 |
| Cyanine 5.5 phosphoramidite | 10-5916 |
| DyLight DY547 phosphoramidite | 10-5917 |
| DyLight DY647 phosphoramidite | 10-5918 |
| Epoch Redmond Red™ phosphoramidite | 10-5920 |
| Epoch Yakima Yellow™ phosphoramidite | 10-5921 |
| Epoch Gig Harbor Green™ phosphoramidite | 10-5922 |
| Epoch Eclipse™ Quencher phosphoramidite | 10-5925 |
| 5'-BHQ-1 phosphoramidite | 10-5931 |
| 5'-BHQ-2 phosphoramidite | 10-5932 |
| 5'-BBQ-650 ®-CE phosphoramidite | 10-5934 |
| BHQ-1-dT | 10-5941 |
| BHQ-2-dT | 10-5942 |
| BBQ-650 ®-dT-CE phosphoramidite | 10-5944 |
| SIMA (HEX)-dT phosphoramidite | 10-5945 |
| 5'-Biotin phosphoramidite | 10-5950 |
| Methylene Blue C3 phosphoramidite | 10-5960 |
| dmf-dG-5'-CE phosphoramidite | 10-9201 |
| Cis-syn Thymine Dimer phosphoramidite | 11-1330 |
| Commercially available from: | |
| Chemgenes Corporation, 33 Industrial Way, | |
| Wilmington, MA, USA | |
| DMT-butane-Diol phosphoramidite | CLP-9775 |
| DMT-dodecane-Diol phosphoramidite | CLP-1114 |
| DMT-ethane-Diol phosphoramidite | CLP-2250 |
| DMT-hexaethyloxy-Glycol phosphoramidite | CLP-9765 |
| DMT-hexane-Diol phosphoramidite | CLP-1120 |
| DMT-nonane-Diol phosphoramidite | CLP-9009 |
| DMT-propane-Diol phosphoramidite | CLP-9908 |
| DMT-tetraethyloxy-Glycol CED phosphoramidite | CLP-1368 |
| DMT-triethyloxy-Glycol phosphoramidite | CLP-1113 |
| Polyethyleneglycol 2000 CED phosphoramidite | CLP-2119 |
| Polyethyleneglycol 4500 CED phosphoramidite | CLP-3118 |
| L-dA (n-bz) CE phosphoramidite | ANP-8031 |
| L-dC (n-acetyl) CE phosphoramidite | ANP-8035 |
| L-dC (n-bz) CE phosphoramidite | ANP-8032 |
| L-dG (n-ibu) CE phosphoramidite | ANP-8033 |
| L-dT CE phosphoramidite | ANP-8034 |

The amidite reagents listed above in Table 1 can be used to insert a reporter unit adjacent to a bulky structure in a modified nucleotide polymer via standard amidite coupling chemistry. That is, each of the phosphoramidite (or phosphonamidite) reagents will react in an amidite coupling reaction with a nucleotide polymer to insert a monomer unit with its particular nucleotide analog structure into the polymer. This resulting reporter unit will comprise from 4 to 25 phosphate (or phosphonate) linkages. Thus, the list of over 300 amidite reagents of Table 1 effectively provides thousands of possible combinations of monomer units that can be synthesized as reporter units in the modified nucleotide polymers of the present disclosure. Thus, it is contemplated that a modified nucleotide polymer of structural formula (I) can include at least barcode unit that includes a reporter unit (R) comprising a nucleotide analog monomer of Table 1 (i.e., resulting from the reaction of the amidite reagent of Table 1).

It should be noted that some of the nucleotide analog monomer units disclosed in Table 1 are also referred to in commercial oligonucleotide synthesis catalogs as "spacers" (e.g., "iSp"), "dyes" (e.g., "iCy3"), or "linkers" (e.g., "hexynyl"). Some of the reporter units described in the examples provided herein are referred to using well-known oligonucleotide synthesis nomenclature (see e.g., the web-site of Integrated DNA Technologies at www.idtdna.com for further details of commonly used oligonucleotide nomenclature). In some embodiments, the reporter units useful in the barcode units of the modified nucleotide polymers (and associated methods of use) of the present disclosure can include any of reporter units exemplified in Example 1, including, but not limited to the group consisting of: dSp, SpC3, SpC6, SpC12, Sp18, Pyrrolidine, spermine, dT-carboxyl, Cy3, dTmp, and combinations thereof.

The design reporter units (e.g., comprising nucleotide analogs from Table 1) for the barcode units of a modified nucleotide polymer can depend on the number of barcode units, the desired nanopore detection characteristics, and the particular method of use. As disclosed in greater detail herein, the modified nucleotide polymers comprising bulky structures and reporter units can be used in methods for detecting and/or quantifying analyte(s) in a solution using a nanopore detection system. A wide range of assay schemes using nanopore detection are contemplated herein. The present disclosure provides examples using modified nucleotide polymers with 3 barcode units comprising duplex sequences (as bulky structure) and 3 distinct various reporter units. The examples demonstrate how to measure the nanopore detection characteristics of different reporter units, specifically different reporter unit currents. Thus, the present disclosure provides the ordinary artisan with tools to prepare modified nucleotide polymers with reporter units that provide different nanopore detectable signals useful across a wide range of assay schemes that use nanopore detection systems.

Spacer Units (X)

Generally, each barcode unit of the modified nucleotide polymers of the present disclosure also include a spacer unit (X) located between a reporter unit and the subsequent bulky structure. The spacer unit generally optimizes the position of reporter units (R) relative to bulky structures (B) in modified nucleotide polymers. Since nanopores may have constrictions or other features that make some regions more sensitive to reporter units than others, in some embodiments it is useful to alter the structure of the modified nucleotide polymer so that the distance between the bulky structure and the reporter unit locates the reporter unit in the region of the nanopore that provides optimal nanopore detection characteristics. Altering the location of the reporting units can be can be carried out by inserting an adjacent chain of phosphodiester or similar building blocks with varying backbone lengths. In some embodiments, the spacer unit can comprise a sequence of natural nucleotides (e.g., $(dT)_{10}$). Each of the natural nucleotides (G, A, T and C) of a DNA polymer spans 6 atoms in the phosphodiester backbone (—P—O—C—C—C—O—) with an approximate length of ~0.72 nm. Insertion of spacer units can provide similarly controlled adjustments of the nucleotide polymer length and thereby adjust the position of the adjacent reporter units.

In some embodiments, a spacer unit can comprise non-natural nucleotide analog units. A wide range of non-natural nucleotide analog monomer units are commercially available as "spacer amidites" reagents which are easily inserted in nucleotide polymers using standard amidite synthesis chemistry. For example, Table 2 (below) provides a range of phosphoramidite reagents that result in spacer units useful to alter the position of reporter units in the modified nucleotide polymers of the present disclosure.

TABLE 2

| Spacer Unit Amidite | Backbone Atoms | Net Charge |
|---|---|---|
| Commercially available from: Glen Research or ChemGenes | | |
| Spacer phosphoramidite 9 (PEG 3) | 11 | −1 |
| Spacer phosphoramidite C3 | 6 | −1 |
| dSpacer CE phosphoramidite | 6 | −1 |
| Spacer phosphoramidite 18 (PEG 6) | 20 | −1 |
| Spacer C12 CE phosphoramidite | 15 | −1 |
| Pyrrolidine-CE phosphoramidite | 6 | 0 |
| Spermine phosphoramidite | 25 | +3 |
| dA-Me Phosphonamidite (Methyl phosphonate backbone) (May also be other nucleotides G, T or C) | 6 | 0 |
| Cyanine 3 phosphoramidite | 16 | 0 |
| Cyanine 5 phosphoramidite | 18 | 0 |
| DMT-butane-Diol phosphoramidite | 7 | −1 |
| DMT-dodecane-Diol phosphoramidite | 15 | −1 |
| DMT-ethane-Diol phosphoramidite | 5 | −1 |
| DMT-hexaethyloxy-Glycol phosphoramidite (PEG 6) | 20 | −1 |
| DMT-hexane-Diol phosphoramidite | 9 | −1 |
| DMT-nonane-Diol phosphoramidite | 12 | −1 |
| DMT-tetraethyloxy-Glycol CED phosphoramidite (PEG 4) | 14 | −1 |
| DMT-triethyloxy-Glycol phosphoramidite (PEG 3) | 11 | −1 |
| Polyethyleneglycol 2000 CED phosphoramidite | ~136 | −1 |
| Polyethyleneglycol 4500 CED phosphoramidite | ~300 | −1 |

In another embodiment, the nanopore detectable modified nucleotide polymer may comprise a structure as described in PCT Publication WO 2015/175789.

Methods for Detecting and/or Quantifying Analytes in Solution Using Modified Nucleotide Polymers and Nanopore Detection Systems The modified nucleotide polymers of the present disclosure can be used in carrying out a wide range of assay methods for detecting and/or quantifying an analyte in a solution wherein the assays utilize nanopore detection. Generally, the methods of the present disclosure rely upon the presence of the reporter units, contained within the barcode units, of the modified nucleotide polymers described herein to provide nanopore detectable blockade currents and/or dwell times upon entering, residing, and/or passing through the nanopore of the nanopore detection system used in the method. Also, the method relies on the ability to associate the modified nucleotide polymers with the desired analyte in the solution to be detected and/or quantified. The method of associating the analyte with the modified nucleotide polymer can include direct associating such as binding of the analyte to the modified nucleotide polymer via specific complementary hybridization (e.g., if the analyte is also a nucleotide polymer), or the method of associating can be indirect such as specific binding of the analyte to an antibody or receptor, and detection of the antibody or receptor via an interaction with the modified nucleotide polymer. In other embodiments, the modified nucleotide polymer is produced via synthesis based on a complementary barcode template. In some embodiments, the modified nucleotide polymer may be synthesized via polymerase extension with nucleotides comprising attached barcode units, as described herein. In other embodiments, the modified nucleotide polymer may be synthesized via ligation of short nucleotide polymers (e.g., 2, 3, 4 or more nucleotides) comprising attached barcode units (e.g., such as those described in US 2011/0251079). After synthesis of the modified nucleotide polymer is completed, it is isolated and then "expanded" (e.g., via chemical, temperature, enzymatic, or other treatment) so that the barcode units may be detected by a nanopore. In a further embodiment, short nucleic acid molecules may be hybridized to the expanded structure to produce the complete nanopore detectable barcode.

In some embodiments, the present disclosure provides a method of detecting and/or quantifying an analyte in a solution, the method comprising: (a) associating the analyte in the solution with any of the modified nucleotide polymers disclosed herein (e.g., a compound of formula (I)); (b) contacting the solution with a nanopore detection system, wherein the system comprises a membrane, an electrode on the cis side and the trans side of the membrane, a nanopore with its pore extending through the membrane, and an electrolyte solution in contact with both electrodes, and wherein the nanopore is under an applied voltage potential; and (c) detecting the one or more blockade currents and/or dwell times produced by the modified nucleotide polymer entering, residing, and/or passing through the nanopore of the nanopore detection system, and thereby detecting and/or quantifying the presence of the analyte associated with the modified nucleotide polymer.

It is contemplated that the general method of the present disclosure for detecting and/or quantifying an analyte can be carried out using any of a wide variety of assay schemes known in the art for detecting an analyte molecule using direct or indirect binding of the analyte to a detectable molecular moiety (e.g., fluorescent label, isotopic label, specific nucleic acid sequence, etc.). In the case of the present methods, the detectable molecular moiety is a modified nucleotide polymer of the present disclosure which can be detected and/or quantified based on its unique blocking current and/or dwell time measured with a nanopore detection system.

A wide variety of nanopore detection systems and associated methods for making them, and using them to detect nucleotide polymers and other molecules are known in the art. See, for example, U.S. patent application Ser. No. 12/308,091, Ju et al., filed May 18, 2009; U.S. patent application Ser. No. 13/994,431, Ju et al., filed Jun. 14, 2013; US Patent Application Publications US 2013/0244340 A1, published Sep. 19, 2013, US 2013/0264207 A1, published Oct. 10, 2013, and US 2014/0134616 A1, published May 14, 2014; PCT International Publication No. PCT/US13/35635, Ju et al., filed Apr. 8, 2013; and PCT International Publication No. PCT/US13/35640, Ju et al., filed Apr. 8, 2013, each of which is hereby incorporated herein by reference in its entirety. The modified nucleotide polymers and associated methods of the present disclosure can be used immediately, no more than ordinary experimentation, with these known nanopore detection system.

In some embodiments, the nanopore detection systems used in the methods described herein may comprise the use of direct current (DC). In other embodiments the method described herein may comprise the use of alternating current (AC). In other embodiments, the system may be operated in Faradaic mode. In other embodiments, the system may be operated in non-Faradaic mode.

It is also contemplated that the general method of the present disclosure for detecting and/or quantifying an analyte can be used to detect and/or quantify any analyte that can bind directly to a nucleic acid, or bind indirectly to a nucleic acid, e.g., bind to another molecule which in turn can bind directly to a nucleic acid. For example, if the analyte is a specific gene sequence (e.g., mRNA or SNP), the sequence modified nucleotide polymer can be designed to bind directly and specifically to it under proper hybridization conditions. The range of analytes which can be detected using the present method, however, is not limited to nucleic acids. It also can include any molecule that can be detected with a specific binding biomolecule (e.g., receptor, antibody, or aptamer), or any specific binding non-biological molecule (e.g., molecularly imprinted polymer, cyclodextrins, nanomaterials), which can itself be detected via selective binding to (or associating with) the modified nucleotide polymers of the present disclosure. For example, an antibody that binds selectively to the analyte of interest may be conjugated to an oligonucleotide (or conjugated to a solid substrate that also has an oligonucleotide bound to it) wherein the oligonucleotide has a sequence that specifically binds to a modified nucleotide polymer.

Accordingly, in one embodiment, the solution containing the analyte further comprises a molecule that specifically binds to the analyte and to the modified nucleotide polymer, and thereby associates the analyte with the modified nucleotide polymer. The selection of the associating molecule will be dependent on the specific analyte that one desires to be detected. In some embodiments, the selection of the associating molecule also can depend on the modified nucleotide polymer.

In some embodiments of the method wherein there is an associating molecule, the step of associating carried out separate from the step of nanopore detection of the modified nucleotide polymer. For example, in some embodiments, the associating step may comprise steps of (a) contacting (and binding) the associating molecule and the analyte, and (b) separating the bound associating molecule-analyte molecule from the sample mixture solution containing the analyte. The solution comprising the separated bound associating molecule-analyte can then be contacted with the modified nucleotide polymer, whereby the analyte becomes associated with the modified nucleotide polymer. This solution comprising the analyte associated modified nucleotide polymer can then be contacted with the nanopore detection system for detection.

Alternatively, in some embodiments, the method can further comprise a step of unbinding the modified nucleotide polymer from the associated analyte and/or associating molecule, and then contacting the modified nucleotide polymer with the nanopore detection system. In such an embodiment, the modified nucleotide polymer is free to enter, reside in, and/or pass through the nanopore of the nanopore detection system without possible interference from the presence of the analyte and/or associating molecule.

As noted above, in some embodiments the method is carried out wherein the step of associating the analyte with the modified nucleotide polymer occurs via binding of the modified nucleotide polymer to the analyte. In some embodiments of the method, the analyte is a nucleotide polymer and the binding of the modified nucleotide polymer to the analyte occurs via hybridization.

Furthermore, it is contemplated that the methods for detecting and/or quantifying an analyte can be carried out in a highly-parallel fashion with multiplex nanopore detection. For example, the above general method of the present disclosure can be performed wherein the nanopore detection system comprises an array of independently addressable nanopores. In such an embodiment, a single sample can be independently measured to detect a single analyte multiple times on the array of nanopore detection systems (i.e., one measurement for each nanopore).

Alternatively, in some embodiments, a single sample can be analyzed on an array of nanopores wherein each nanopore may detect and/or quantify a different analyte or set of analytes. In such embodiments, it is contemplated that the method is carried out using a composition of a set of different modified nucleotide polymers, wherein each different modified nucleotide polymer produces different detectable blockade currents and/or dwell times upon entering, residing, and/or passing through a nanopore that is under an applied voltage potential, wherein the different detectable blockade currents and/or dwell times can distinguish the different modified nucleotide polymers.

Accordingly, in some embodiments the method of detecting and/or quantifying an analyte may be carried out wherein the solution comprises a plurality of analytes each of which is associated with a different modified nucleotide polymer of formula (I), wherein each of the different modified nucleotide polymers of formula (I) produces different detectable blockade currents and/or dwell times upon entering, residing, and/or passing through a nanopore that is under an applied voltage potential, whereby the different detectable blockade currents and/or dwell times can detectably distinguish the different modified nucleotide polymers and their associated analytes. In some embodiments, the method of detecting a plurality of analytes can be carried wherein the nanopore detection system comprises an array of independently addressable nanopores.

In some embodiments, a nanopore detectable modified nucleotide polymer is created as the last step in an amplification method using a primer sequence as the template to create the nanopore detectable modified nucleotide polymer; in other embodiments, a unique barcode sequence is used as the template to create the barcode. In other embodiments, nanopore detectable modified nucleotide polymers are synthesized independently and attached to oligonucleotide primers used in a method described herein (e.g., an amplification method such as PCR). In other embodiments, nanopore detectable modified nucleotide polymer may be created across exon-intron boundaries, across introns, or across chromosome breakpoints or translocation sites.

Nanopore detectable modified nucleotide polymers as described herein may also be used, for example, to detect analytes such as proteins. In one embodiment, for example, a nanopore detectable modified nucleotide polymer may be attached to a polypeptide such as an antibody or other binding protein. The antibody is contacted with a test analyte, and bound antibody is separated and then detected using a nanopore as described herein. Nanopore detectable modified nucleotide polymers may be attached to other molecules (e.g., polypeptides or nucleic acids) using any appropriate method known in the art. In one embodiment, nanopore detectable modified nucleotide polymers are attached using click chemistry.

Additional description of methods for which the nanopore detectable modified nucleotide polymers described herein may be found, for example, in publications, US 2012/0034685 and US 2014/0349859. Further methods are well-known to those skilled in the art.

In further embodiments, the nanopore detectable modified nucleotide polymers described herein may be used as indexes to identify molecules based on, for example, their source. For example, in a multiplexed assay comprising samples from multiple different subjects, each sample can be indexed based on a different barcode sequence. In such a method, adapters containing a unique barcode template and a universal primer may be added to each sample. After mixing the samples, the original sample of origin can be identified and detected using a nanopore detectable barcode. Other uses of the disclosed nanopore detectable barcodes may be to identify different loci, different strands, or any parameter envisioned by one of skill in the art.

EXAMPLES

Example 1: Nanopore Detection of Barcodes Using Modified Nucleotide Polymers Comprising Three Barcode Units This example illustrates nanopore detection of a three different barcodes corresponding to three modified nucleotide polymers each having three barcode units comprising a bulky structure, an adjacent reporter unit comprising four nucleotide or nucleotide analog monomer units, a $dT_{10}$ monomer spacer, and a tail unit comprising a homopolymer $dT_{20}$ sequence.

The three specific modified nucleotide polymers used are shown FIGS. 2A, 2B, and 2C. The three single-stranded polymers were prepared using standard automated oligonucleotide synthesis methods incorporating the nucleotide analog monomer units in the reporter units using commercially available amidite reagents.

The bulky structure duplex regions of the modified nucleotide polymers were formed prior to use by annealing the single-stranded modified nucleotide polymer with an 8-mer oligonucleotide 5'-CGGCGGCG-3' (3'-GCGGCGGC-5'). This oligonucleotide is complementary to the bulky structure sequence 5'-CGCCGCCG-3'. Annealing to form the bulky structure duplex regions was carried out by dissolving in electrolyte and adding a 10% excess of the 8-mer oligonucleotide, heating for 2 min at 85° C. and cooling to 4° C.

As shown in FIG. 1, each of the three modified nucleotide polymers comprises three barcode units capable and providing three different nanopore-detectable barcodes denoted XYZ (FIG. 1A), WYZ (FIG. 1B), and WXZ (FIG. 1C). The specific nucleotide or nucleotide analog monomer units making up the 4-mer sequences of the different barcode units are shown in the Reporter Unit Key in FIG. 1D. Also shown are the predicted nanopore detectable current levels for a reporter unit comprising a 4-mer of each of the monomers used: W (i.e., (Pyrrolidine)$_4$), X (i.e., (dTmp)$_4$), Y (i.e., (dT$_4$)), and Z (i.e., (SpC3)$_4$). The corresponding predicted nanopore-detected current levels representing the barcodes are shown in FIG. 2A, FIG. 3A, and FIG. 4A.

All nanopore current-time recordings were carried out on a Genia integrated circuit (I) chip-station (Genia Technologies, Mountain View, Calif.). The nanopore array consists of a 131,072 sensor semiconductor integrated circuit in a simple fluidics package interfaced with the Genia Reader computer. The chip is manufactured with surface modifications to allow for constant contact with biological reagents and conductive salt solutions. Each Ag electrode sensor on the chip is individually controlled and monitored and isolated in a well, allowing independent measurement.

The lipid used for phospholipid bilayer formation was 1,2-diphytanoyl-sn-glycero-3-phosphocholine, powder (Avanti Polar Lipids). This powder was dissolved in decane at a concentration of 15 mg/mL before use. Lipid bilayers were formed by an automatic pumping process adding lipid solution, electrolyte and air bubbles resulting in single bilayer membranes sealed over the electrodes.

A 15 µL mixture containing 0.05 µg of purified α-hemolysin with 15 µM of modified nucleotide polymer in electrolyte was pumped into the chip. α-HL pores formed spontaneously or with electrical stimulation under computer control. Voltage was applied as a series of pulses typically lasting 2-5 seconds at 180 mV. Under these conditions, single open pores passed ~55 pA. Measurements of current across the nanopores were carried out in 300 mM KCl, 20 mM Hepes, pH 7.5 as the electrolyte solution. Currents were recorded and analyzed using custom software and manually scanned for the multiple-level capture patterns expected. All experiments were conducted at 20° C.

Results

FIGS. 2B, 3B, and 4B show representative plots of nanopore current levels versus time measured for each of the three modified nucleotide polymers designed to provide the barcodes XYZ, WYZ, and WXZ, respectively. Each of the barcode patterns was detectable over the background nanopore current and correlated well with the predicted patterns of FIGS. 2A, 3B, and 4B.

Figure 5A:
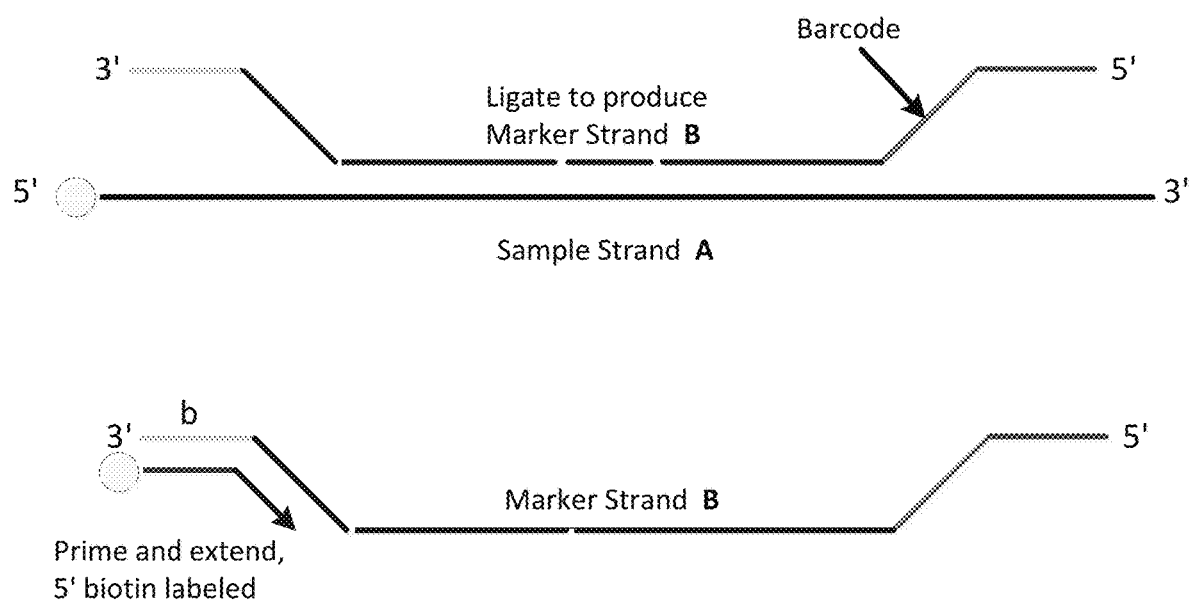
Figure 5B:
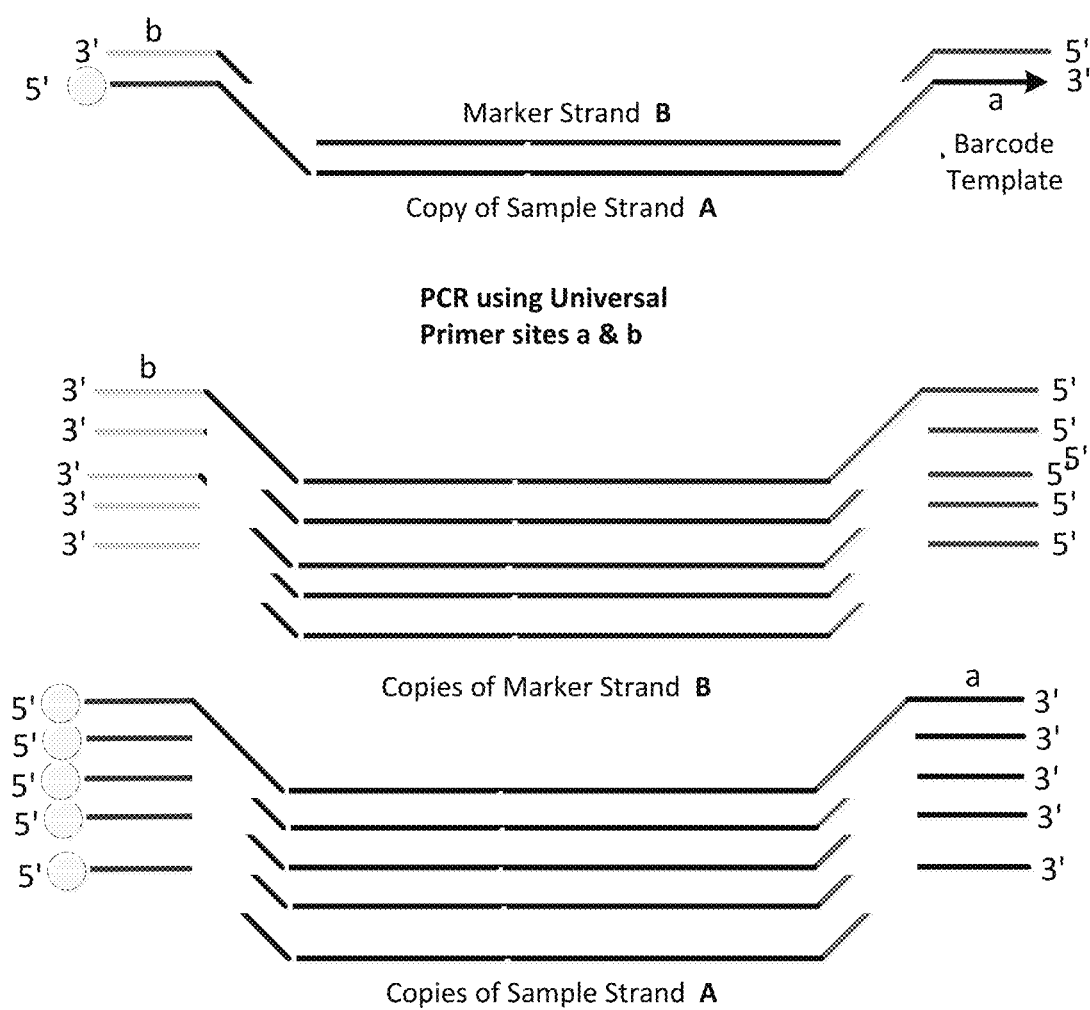
Figure 5C:
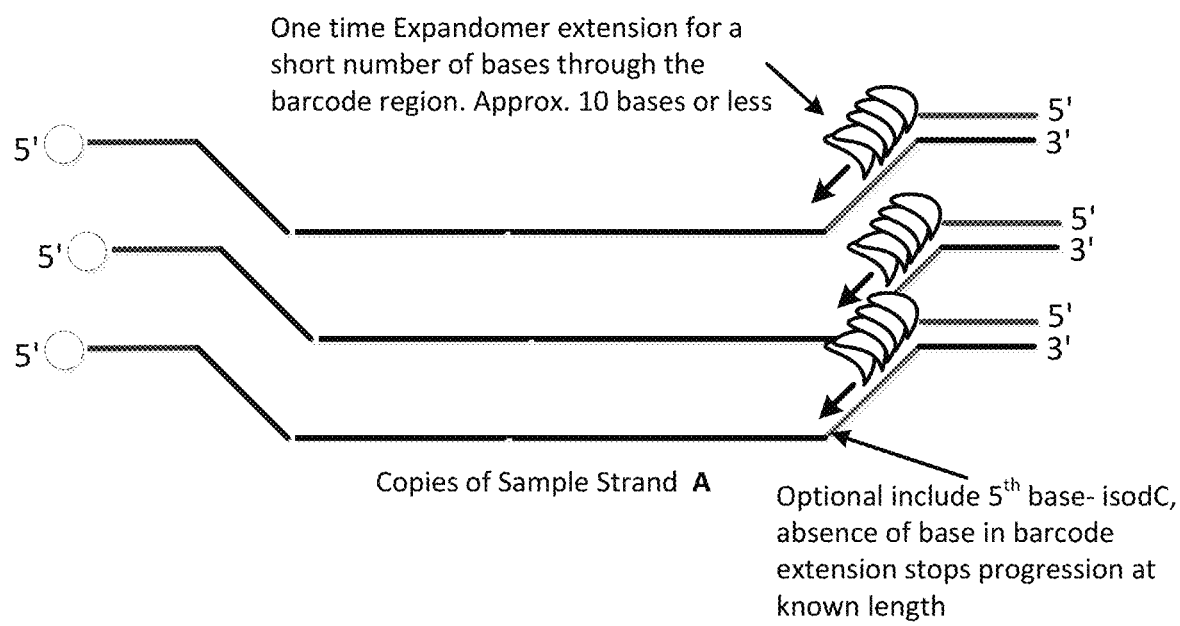
Figure 5D:
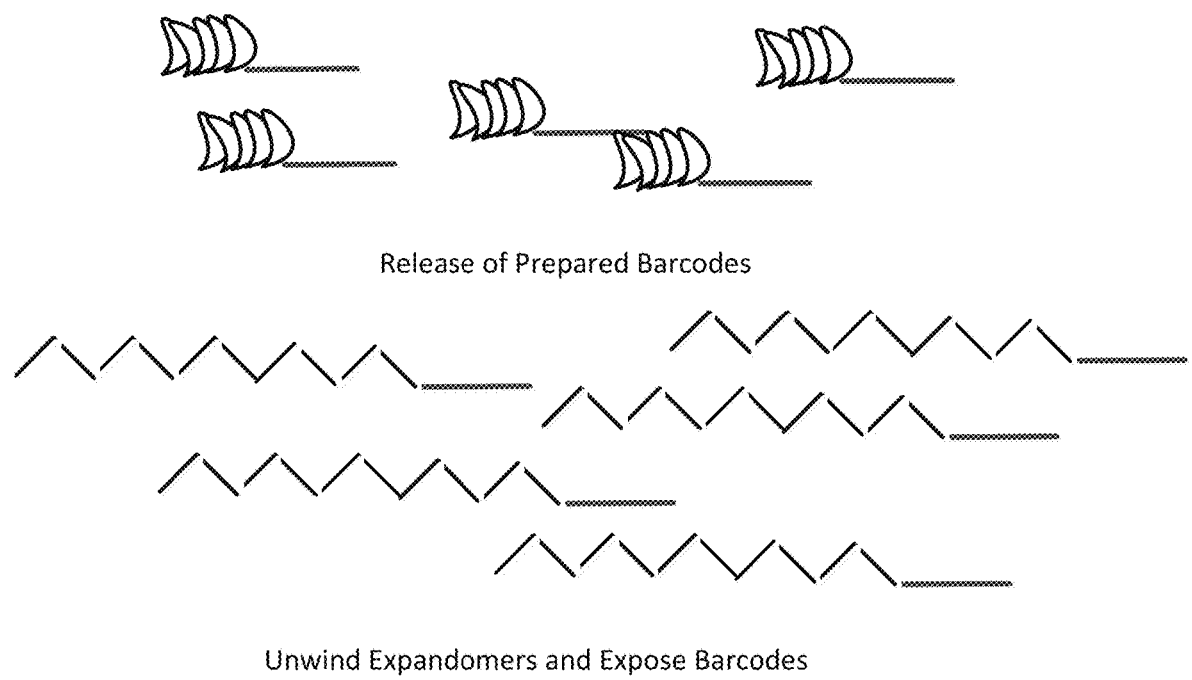
Figure 6:
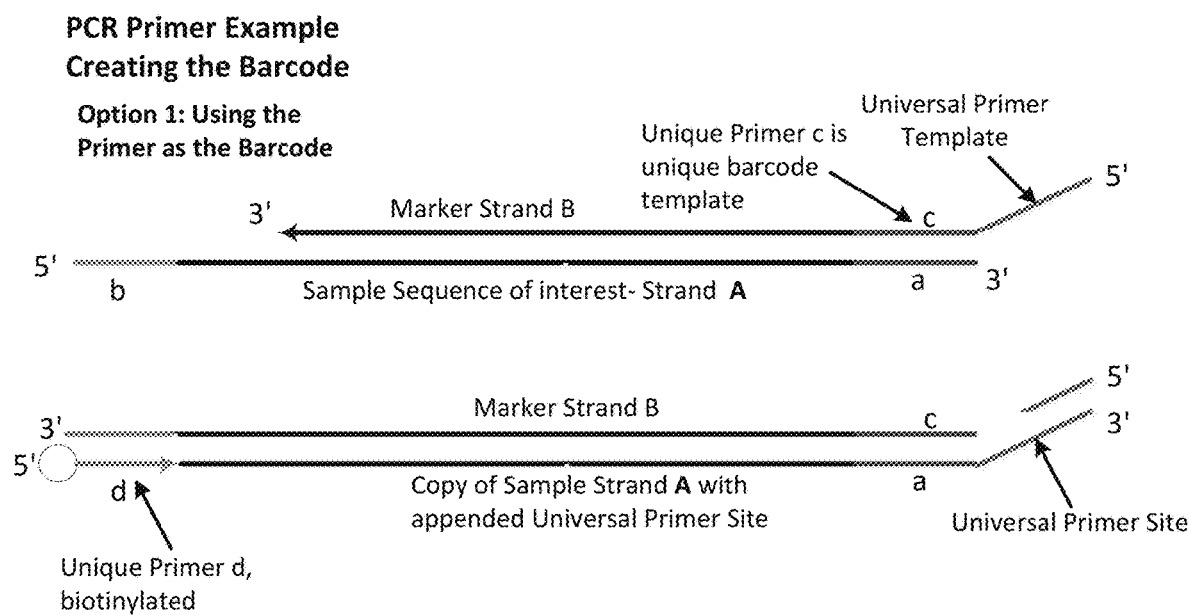
FIG. 6 depicts the use of nanopore-detectable barcodes using the primer sequence as the unique barcode template for PCR.
Figure 9:
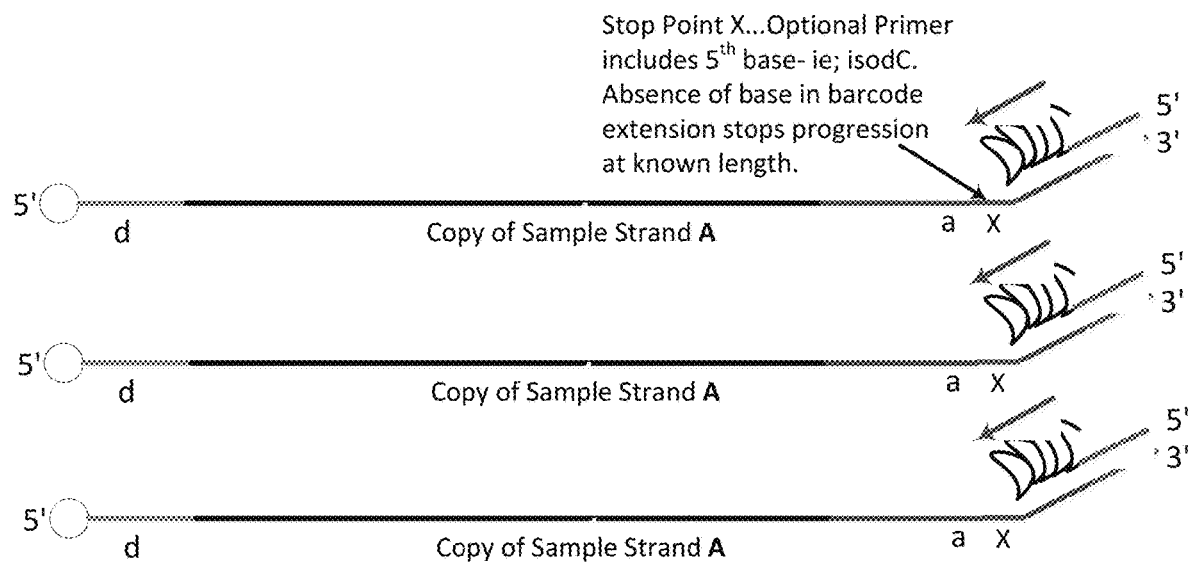
FIG. 9 depicts the initiation of a unique barcode read by a universal primer.
Figure 10:
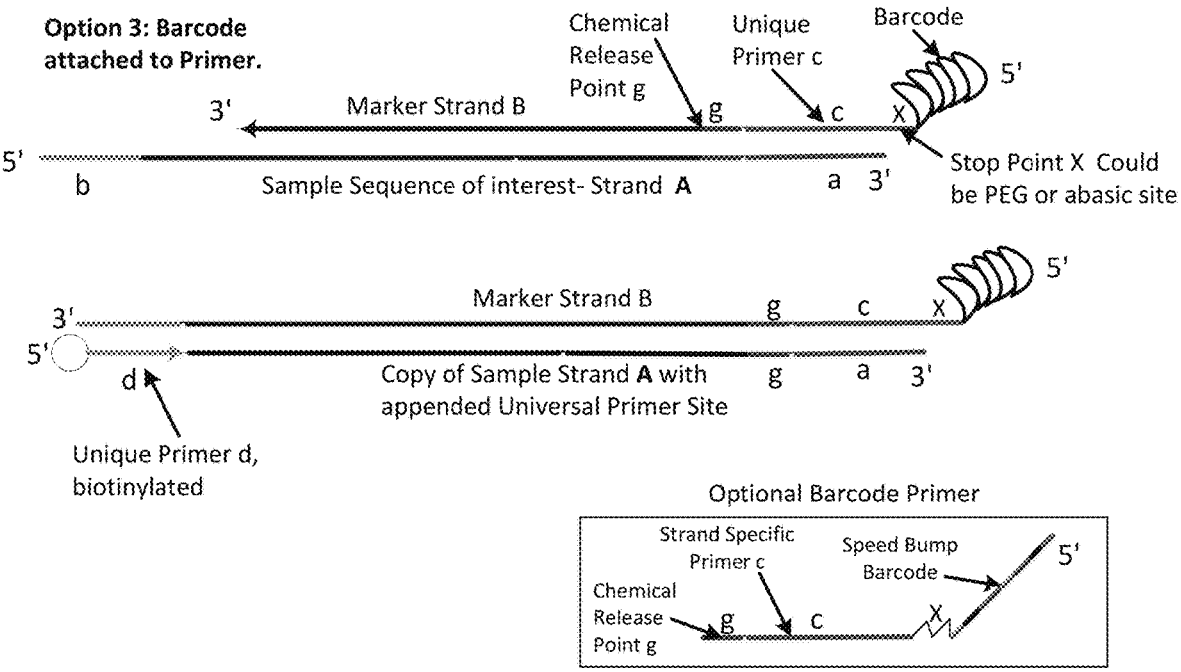
FIG. 10 depicts PCR detection with a pre-made barcode attached to a primer.
Figure 13:
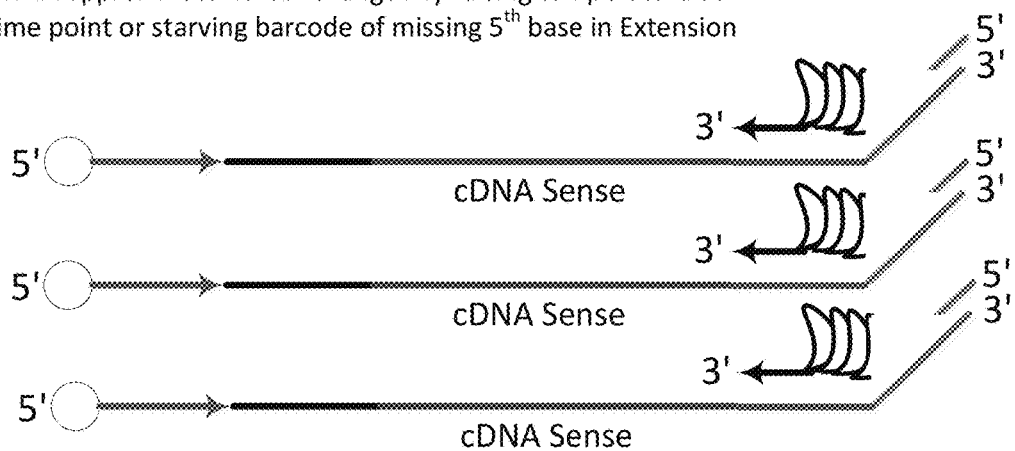
FIG. 13 depicts expression analysis using nanopore-detectable barcodes, with a read into an intron sequence, and the barcode template in the primer.
Figure 14:
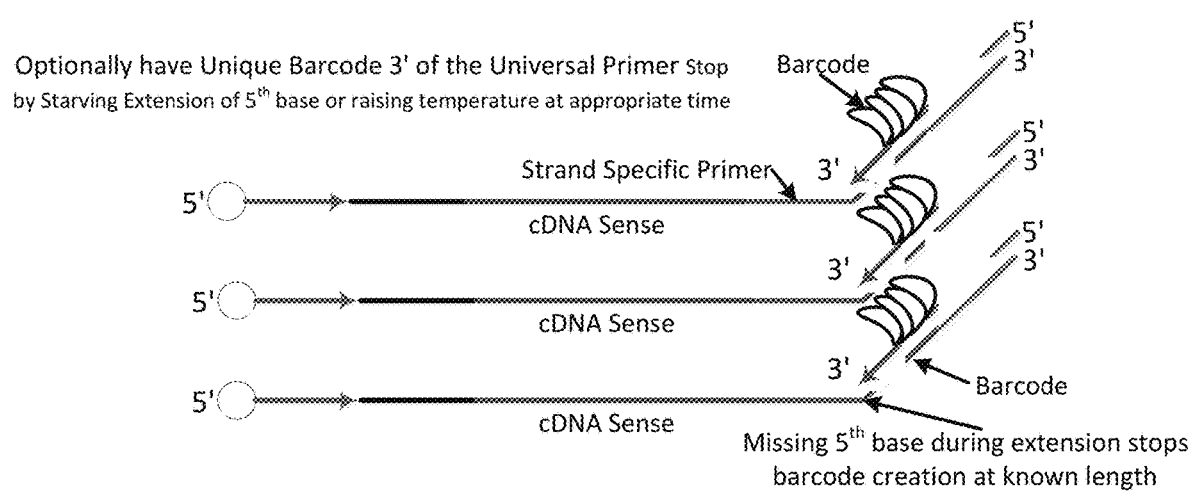
FIG. 14 depicts expression analysis using nanopore-detectable barcodes, with a universal primer that initiates barcode synthesis.
Figure 16:
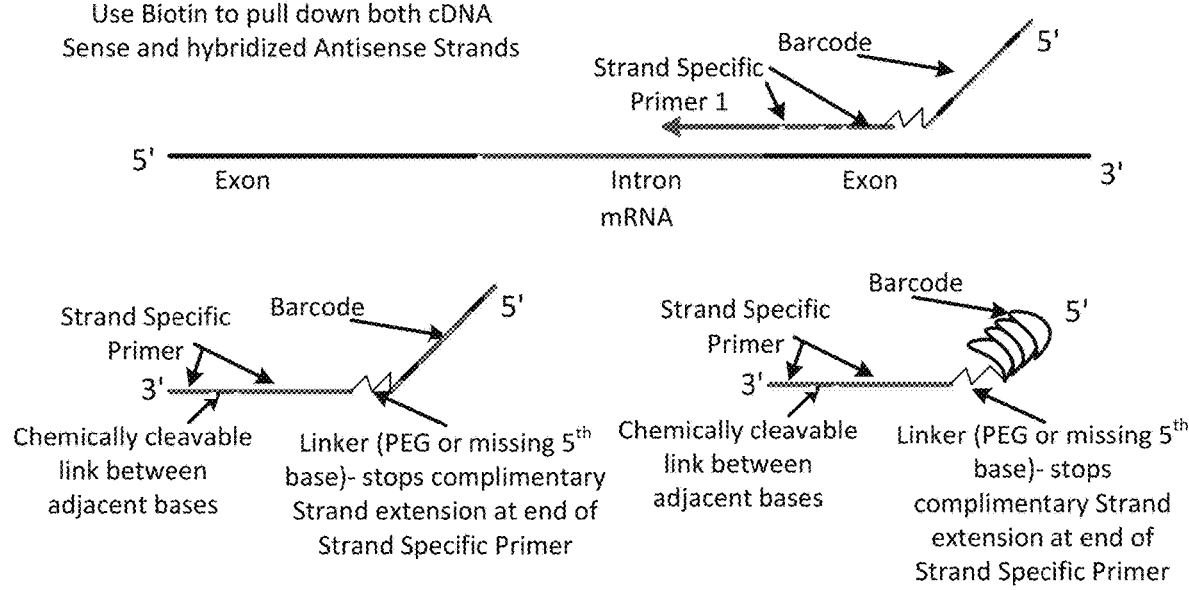
FIG. 16 depicts expression analysis using premade nanopore-detectable barcodes attached to a primer.
Figure 17:
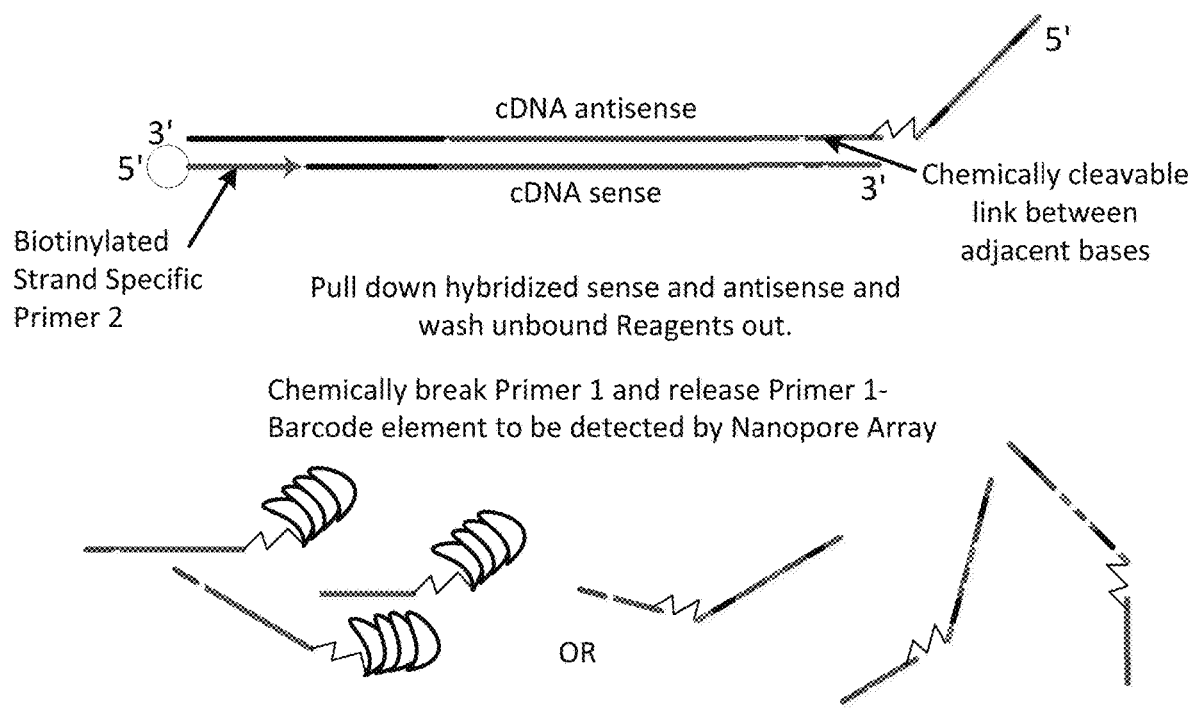
FIG. 17 depicts expression analysis using premade nanopore-detectable barcodes attached to a primer.
Figure 18:
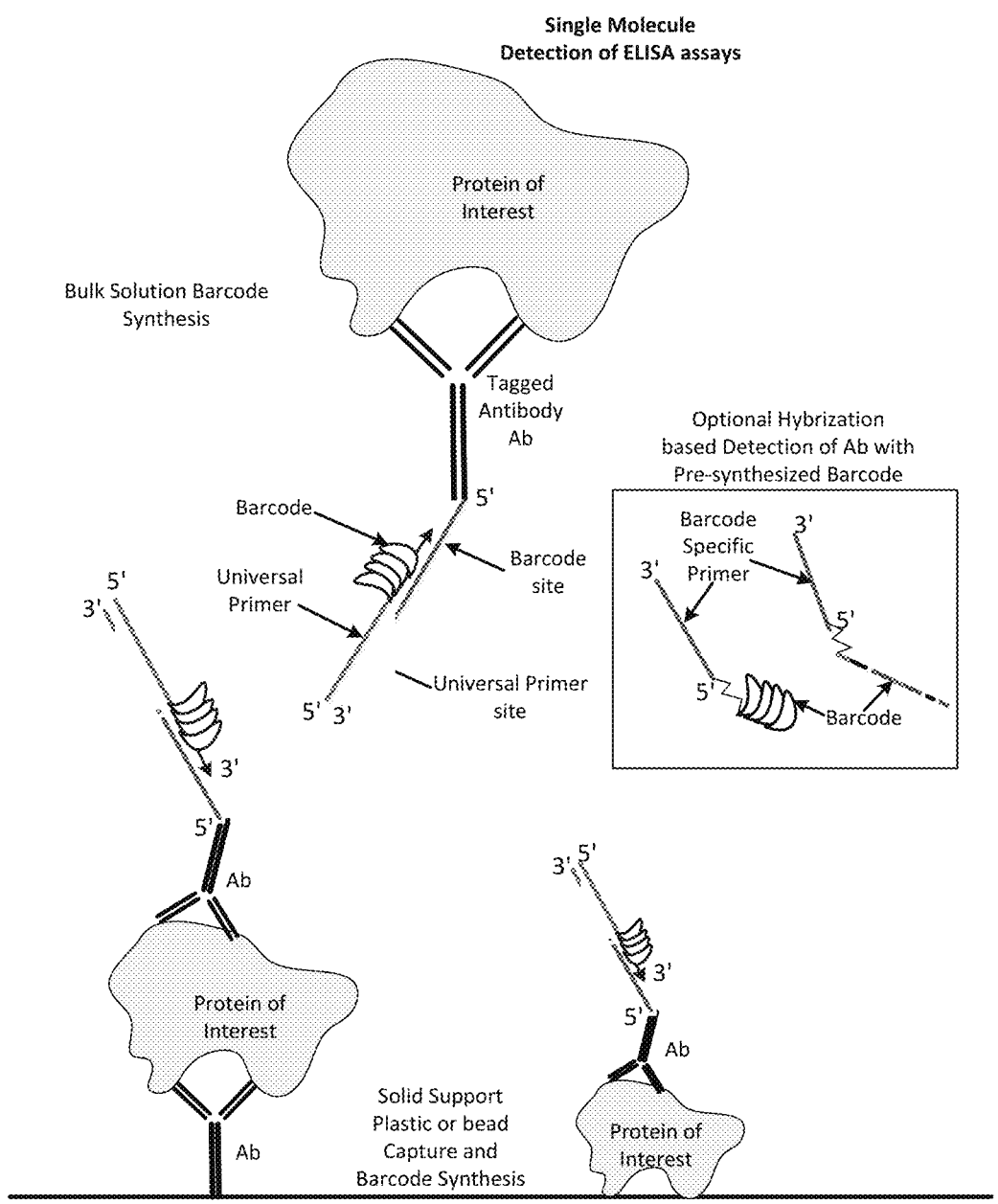
FIG. 18 depicts protein detection using nanopore-detectable barcodes.

Example 2: Detection and Counting of Nucleic Acid Molecules Using Nanopore Detectable Barcodes FIGS. 5A-5B depict a method to create nanopore detectable modified nucleotide polymers to detect and/or count the presence of DNA molecules in a sample. A target sample strand A is contacted with three oligonucleotides (a lefthand primer, a righthand primer, and a bridging oligonucleotide) that hybridize specifically to adjacent sites on the target strand. The hybridized oligonucleotides are then ligated and amplified using universal priming sites. The lefthand primer may comprise a biotin moiety, which allows isolation of marker strand B via binding to streptavidin. The righthand primer comprises a barcode template disposed between the universal priming site and the specifically hybridized region. After amplification, the marker stand B is isolated, and the nanopore detectable modified nucleotide polymer is synthesized using polymerase extension with modified nucleotides with attached barcode units. The end of the barcode template region may comprise a modified nucleotide such as isodC, so that extension stops (due to absence of complementary nucleotide during synthesis). After completion of synthesis, the nanopore detectable modified nucleotide polymers are separated from the marker strand, expanded, and read by the nanopore (FIG. 5D-5E).

FIGS. 6-20 depict further specific embodiments of the use of nanopore detectable modified nucleotide polymers disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

[Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The invention claimed is:

1. A method for detecting and/or quantifying a target nucleic acid molecule, the method comprising:
   a. contacting the target nucleic acid molecule with at least one primer that specifically hybridizes to the target nucleic acid molecule, resulting in a target nucleic acid molecule-primer complex;
   b. extending the primer using modified nucleotides, wherein the modified nucleotides comprise:
      i. nucleotides comprising attached barcode units, or
      ii. short expandable nucleotide polymers comprising barcode units attached to 2, 3, 4, or more nucleotides, and wherein the barcode units each comprise at least two bulky structures, and wherein each bulky structure is adjacent to a reporter sequence,
   to produce a complex comprising the target nucleic acid molecule and a modified nucleotide polymer;
   c. isolating the modified nucleotide polymer;
   d. detecting and/or quantifying the modified nucleotide polymer using a nanopore.

2. The method of claim 1, wherein the target nucleic acid molecule is selected from the group consisting of mRNA or cDNA.

3. The method of any of claim 2, wherein the primer comprises oligo-dT.

4. The method of claim 2, wherein the nucleic acid molecule is DNA.

5. The method of claim 1, wherein the nucleic acid molecule is amplified.

6. A method for detecting and/or quantifying a target nucleic acid molecule, the method comprising:
   a. contacting the target nucleic acid molecule with at least a first primer and a second primer, wherein:
      i. each primer comprises a target-specific region and a universal priming site;
      ii. the second primer comprises a barcode coding region disposed between its target-specific region and its universal priming site;
   b. amplifying the target nucleic acid molecule to produce amplicons;
   c. isolating and denaturing the amplicons to produce single-stranded amplicons;
   d. contacting the single-stranded amplicons with the second primer;
   e. extending the second primer using modified nucleotides, wherein the modified nucleotides comprise:
      i. nucleotides comprising attached barcode units, or
      ii. short expandable nucleotide polymers comprising barcode units attached to 2, 3, 4, or more nucleotides, and wherein the barcode units each comprise at least two bulky structures, and wherein each bulky structure is adjacent to a reporter sequence,
   to produce an amplicon-modified nucleotide polymer complex;
   f. isolating the modified nucleotide polymer;
   g. detecting and/or quantifying the modified nucleotide polymer using a nanopore.

7. A multiplexed method for detecting and/or quantitating nucleic acid target molecules in a sample, comprising the steps of:
   a. contacting sample with a set of at least two oligonucleotide primers, wherein at least one primer in each set comprises a barcode template, wherein each primer comprises a universal priming sequence, and wherein the oligonucleotide primers hybridize at adjacent sites on the target nucleic acid molecules;
   b. ligating the primers;
   c. amplifying the ligated nucleic acid molecules;
   d. extending the second primer using modified nucleotides, wherein the modified nucleotides comprise:
      i. nucleotides comprising attached barcode units, or
      ii. short expandable nucleotide polymers comprising barcode units attached to 2, 3, 4, or more nucleotides, and wherein the barcode units each comprise at least two bulky structures, and wherein each bulky structure is adjacent to a reporter sequence,
   to produce an amplicon-modified nucleotide polymer complex;
   e. isolating the modified nucleotide polymer;
   f. detecting and/or quantifying the modified nucleotide polymer using a nanopore.

8. The method of claim 7, wherein the barcode template comprises a sample index, a locus index, or a strand index.

9. A method of detecting an analyte in a sample, comprising the steps of:
   a. contacting the sample with a specific binding protein comprising a nanopore detectable barcode to produce an analyte-binding protein complex, wherein the nanopore detectable barcode comprises a modified nucleic acid polymer comprising at least two bulky structures, and wherein each bulky structure is adjacent to a reporter sequence;
   b. isolating the analyte-binding protein complex;
   c. detecting the nanopore detectable barcode using a nanopore.

10. The method of claim 9, wherein the specific binding protein is an antibody.

11. The method of any claim 9, wherein the nanopore-detectable barcode is attached to the specific binding protein using click chemistry.

12. The method of any claim 10, wherein the nanopore-detectable barcode is attached to the specific binding protein using click chemistry.

* * * * *

SEQUENCE LISTING

```
<160> NUMBER OF SEQ ID NOS: 4

<210> SEQ ID NO 1
<211> LENGTH: 86
<212> TYPE: DNA
<213> ORGANISM: Artificial Sequence
<220> FEATURE:
<223> OTHER INFORMATION: Modified nucleotide polymer
<220> FEATURE:
<221> NAME/KEY: misc_feature
<222> LOCATION: (9)..(9)
<223> OTHER INFORMATION: dT-methyl phosphonate
<220> FEATURE:
<221> NAME/KEY: misc_feature
<222> LOCATION: (10)..(10)
<223> OTHER INFORMATION: dT-methyl phosphonate
<220> FEATURE:
<221> NAME/KEY: misc_feature
<222> LOCATION: (11)..(11)
<223> OTHER INFORMATION: dT-methyl phosphonate
<220> FEATURE:
<221> NAME/KEY: misc_feature
<222> LOCATION: (12)..(12)
```

<223> OTHER INFORMATION: dT-methyl phosphonate
<220> FEATURE:
<221> NAME/KEY: misc_feature
<222> LOCATION: (31)..(31)
<223> OTHER INFORMATION: dT
<220> FEATURE:
<221> NAME/KEY: misc_feature
<222> LOCATION: (32)..(32)
<223> OTHER INFORMATION: dT
<220> FEATURE:
<221> NAME/KEY: misc_feature
<222> LOCATION: (33)..(33)
<223> OTHER INFORMATION: dT
<220> FEATURE:
<221> NAME/KEY: misc_feature
<222> LOCATION: (34)..(34)
<223> OTHER INFORMATION: dT
<220> FEATURE:
<221> NAME/KEY: misc_feature
<222> LOCATION: (53)..(53)
<223> OTHER INFORMATION: SpC3 (propyl spacer)
<220> FEATURE:
<221> NAME/KEY: misc_feature
<222> LOCATION: (54)..(54)
<223> OTHER INFORMATION: SpC3 (propyl spacer)
<220> FEATURE:
<221> NAME/KEY: misc_feature
<222> LOCATION: (55)..(55)
<223> OTHER INFORMATION: SpC3 (propyl spacer)
<220> FEATURE:
<221> NAME/KEY: misc_feature
<222> LOCATION: (56)..(56)
<223> OTHER INFORMATION: SpC3 (propyl spacer)

<400> SEQUENCE: 1
cgccgccgnn nnttttttt tcgccgccg nnnnttttt ttttcgccgc cgnnnntttt      60
tttttttttt tttttttttt tttttt                                       86

<210> SEQ ID NO 2
<211> LENGTH: 86
<212> TYPE: DNA
<213> ORGANISM: Artificial Sequence
<220> FEATURE:
<223> OTHER INFORMATION: Modified nucleotide polymer
<220> FEATURE:
<221> NAME/KEY: misc_feature
<222> LOCATION: (9)..(9)
<223> OTHER INFORMATION: Pyrrolidine
<220> FEATURE:
<221> NAME/KEY: misc_feature
<222> LOCATION: (10)..(10)
<223> OTHER INFORMATION: Pyrrolidine
<220> FEATURE:
<221> NAME/KEY: misc_feature
<222> LOCATION: (11)..(11)
<223> OTHER INFORMATION: Pyrrolidine
<220> FEATURE:
<221> NAME/KEY: misc_feature
<222> LOCATION: (12)..(12)
<223> OTHER INFORMATION: Pyrrolidine
<220> FEATURE:
<221> NAME/KEY: misc_feature
<222> LOCATION: (31)..(31)
<223> OTHER INFORMATION: dT
<220> FEATURE:
<221> NAME/KEY: misc_feature
<222> LOCATION: (32)..(32)
<223> OTHER INFORMATION: dT
<220> FEATURE:
<221> NAME/KEY: misc_feature
<222> LOCATION: (33)..(33)
<223> OTHER INFORMATION: dT
<220> FEATURE:
<221> NAME/KEY: misc_feature
<222> LOCATION: (34)..(34)
<223> OTHER INFORMATION: dT

```
<220> FEATURE:
<221> NAME/KEY: misc_feature
<222> LOCATION: (53)..(53)
<223> OTHER INFORMATION: SpC3 (propyl spacer)
<220> FEATURE:
<221> NAME/KEY: misc_feature
<222> LOCATION: (54)..(54)
<223> OTHER INFORMATION: SpC3 (propyl spacer)
<220> FEATURE:
<221> NAME/KEY: misc_feature
<222> LOCATION: (55)..(55)
<223> OTHER INFORMATION: SpC3 (propyl spacer)
<220> FEATURE:
<221> NAME/KEY: misc_feature
<222> LOCATION: (56)..(56)
<223> OTHER INFORMATION: SpC3 (propyl spacer)

<400> SEQUENCE: 2
cgccgccgnn nnttttttt ttcgccgccg nnnnttttt ttttcgccgc cgnnnntttt      60 ttttttttt ttttttttt ttttt                                            86

<210> SEQ ID NO 3
<211> LENGTH: 86
<212> TYPE: DNA
<213> ORGANISM: Artificial Sequence
<220> FEATURE:
<223> OTHER INFORMATION: Modified nucleotide polymer
<220> FEATURE:
<221> NAME/KEY: misc_feature
<222> LOCATION: (9)..(9)
<223> OTHER INFORMATION: Pyrrolidine
<220> FEATURE:
<221> NAME/KEY: misc_feature
<222> LOCATION: (10)..(10)
<223> OTHER INFORMATION: Pyrrolidine
<220> FEATURE:
<221> NAME/KEY: misc_feature
<222> LOCATION: (11)..(11)
<223> OTHER INFORMATION: Pyrrolidine
<220> FEATURE:
<221> NAME/KEY: misc_feature
<222> LOCATION: (12)..(12)
<223> OTHER INFORMATION: Pyrrolidine
<220> FEATURE:
<221> NAME/KEY: misc_feature
<222> LOCATION: (31)..(31)
<223> OTHER INFORMATION: dT-methyl phosphonate
<220> FEATURE:
<221> NAME/KEY: misc_feature
<222> LOCATION: (32)..(32)
<223> OTHER INFORMATION: dT-methyl phosphonate
<220> FEATURE:
<221> NAME/KEY: misc_feature
<222> LOCATION: (33)..(33)
<223> OTHER INFORMATION: dT-methyl phosphonate
<220> FEATURE:
<221> NAME/KEY: misc_feature
<222> LOCATION: (34)..(34)
<223> OTHER INFORMATION: dT-methyl phosphonate
<220> FEATURE:
<221> NAME/KEY: misc_feature
<222> LOCATION: (53)..(53)
<223> OTHER INFORMATION: SpC3 (propyl spacer)
<220> FEATURE:
<221> NAME/KEY: misc_feature
<222> LOCATION: (54)..(54)
<223> OTHER INFORMATION: SpC3 (propyl spacer)
<220> FEATURE:
<221> NAME/KEY: misc_feature
<222> LOCATION: (55)..(55)
<223> OTHER INFORMATION: SpC3 (propyl spacer)
<220> FEATURE:
<221> NAME/KEY: misc_feature
<222> LOCATION: (56)..(56)
<223> OTHER INFORMATION: SpC3 (propyl spacer)
```

```
<400> SEQUENCE: 3
cgccgccgnn nntttttttt ttcgccgccg nnnnttttt ttttcgccgc cgnnnntttt        60
tttttttttt tttttttttt tttttt                                           86

<210> SEQ ID NO 4
<211> LENGTH: 18
<212> TYPE: DNA
<213> ORGANISM: Artificial Sequence
<220> FEATURE:
<223> OTHER INFORMATION: Hairpin-forming sequence

<400> SEQUENCE: 4
gcggcgcgta agcgccgc                                                    18
```